United States Patent
Craighead et al.

(10) Patent No.: US 6,753,200 B2
(45) Date of Patent: Jun. 22, 2004

(54) MONOLITHIC NANOFLUID SIEVING STRUCTURES FOR DNA MANIPULATION

(75) Inventors: Harold G. Craighead, Ithaca, NY (US); Stephen W. Turner, Ithaca, NY (US)

(73) Assignee: Cornell Research Foundation, Ithaca, NY (US)

( * ) Notice: Subject to any disclaimer, the term of this patent is extended or adjusted under 35 U.S.C. 154(b) by 0 days.

(21) Appl. No.: 09/905,027

(22) Filed: Jul. 13, 2001

(65) Prior Publication Data

US 2002/0072243 A1 Jun. 13, 2002

Related U.S. Application Data

(63) Continuation of application No. PCT/US00/00013, filed on Jan. 12, 2000.
(60) Provisional application No. 60/115,854, filed on Jan. 13, 1999.

(51) Int. Cl.[7] ............................................. H01L 21/00
(52) U.S. Cl. ........................... 438/48; 438/50; 438/53; 438/800
(58) Field of Search ............................... 438/753, 800, 438/53, 48, 745, 50

(56) References Cited

U.S. PATENT DOCUMENTS

| | | | |
|---|---|---|---|
| 4,698,407 A | * 10/1987 | Nakagima et al. | 528/14 |
| 5,137,618 A | 8/1992 | Burnett et al. | 205/125 |
| 5,258,097 A | * 11/1993 | Mastrangelo | 216/39 |
| 5,591,139 A | * 1/1997 | Lin et al. | 604/264 |
| 5,660,680 A | 8/1997 | Keller | 438/50 |
| 5,950,091 A | 9/1999 | Fulford et al. | 438/303 |
| 5,966,600 A | 10/1999 | Hong | 438/253 |
| 6,136,212 A | * 10/2000 | Mastrangelo et al. | 216/27 |
| 6,146,543 A | * 11/2000 | Tai et al. | 216/2 |
| 2001/0005527 A1 | * 6/2001 | Vaeth | 422/100 |

* cited by examiner

*Primary Examiner*—Michael Trinh
(74) *Attorney, Agent, or Firm*—Schwegman, Lundberg, Woessner & Kluth, P.A.

(57) ABSTRACT

A new technique for fabricating two-dimensional and three-dimensional fluid microchannels for molecular studies includes fabricating a monolithic unit using planar processing techniques adapted from semiconductor electronics fabrication. A fluid gap between a floor layer (12) and a ceiling layer (20) is provided by an intermediate patterned sacrificial layer (14) which is removed by a wet chemical etch. The process may be used to produce a structure such as a filter or artificial gel by using Electron beam lithography to define a square array of 100 nm holes (30) in the sacrificial layer. CVD silicon nitride (54) is applied over the sacrificial layer and enters the array of holes to produce closely spaced pillars. The sacrificial layer can be removed with a wet chemical etch trough access holes in the ceiling layer, after which the access holes are sealed with VLTO silicon dioxide (64).

24 Claims, 19 Drawing Sheets

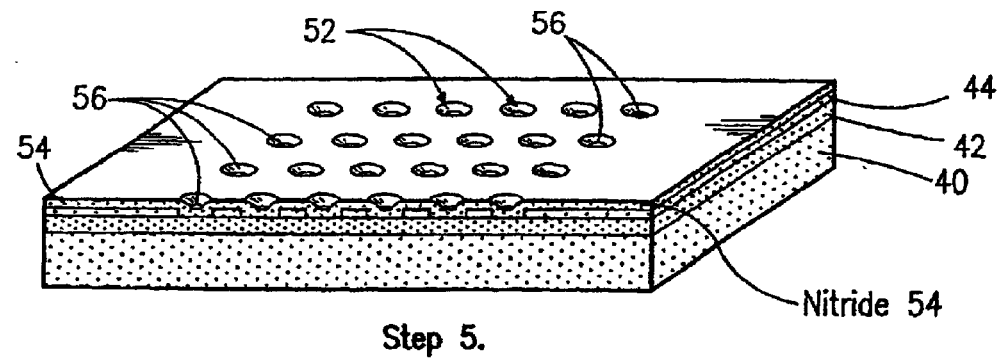
Step 5.
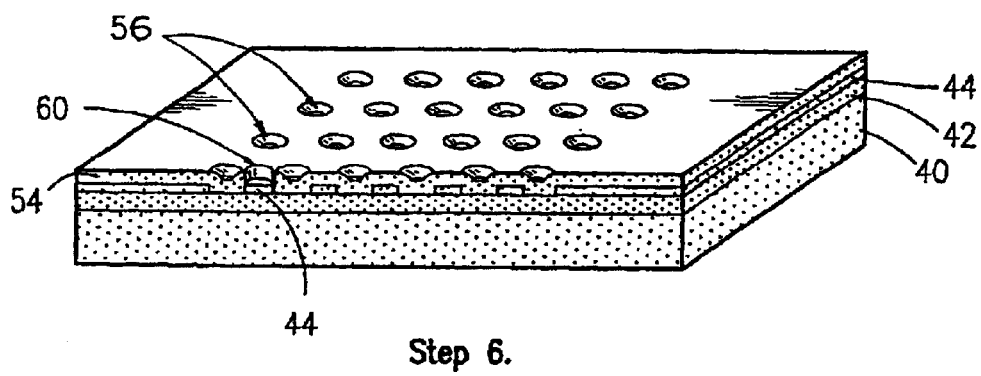
Step 6.
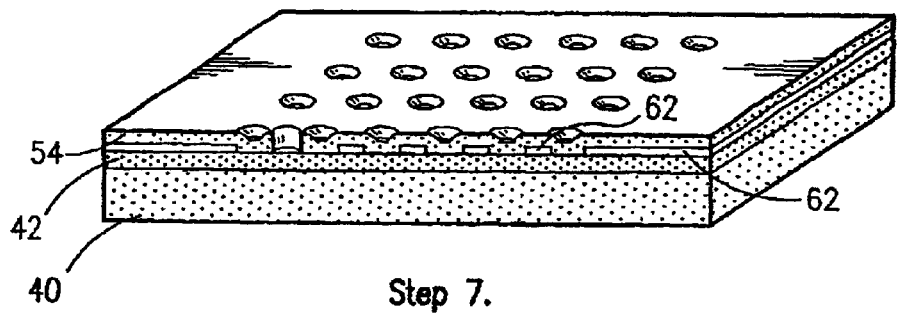
Step 7.
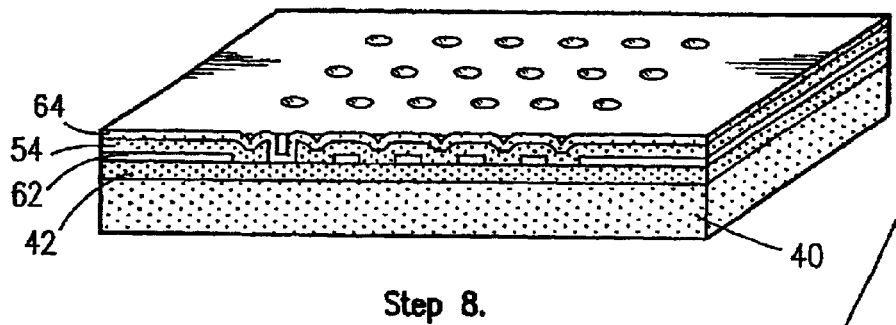
Step 8.
FIG.4(b)

FIG. 6(a)
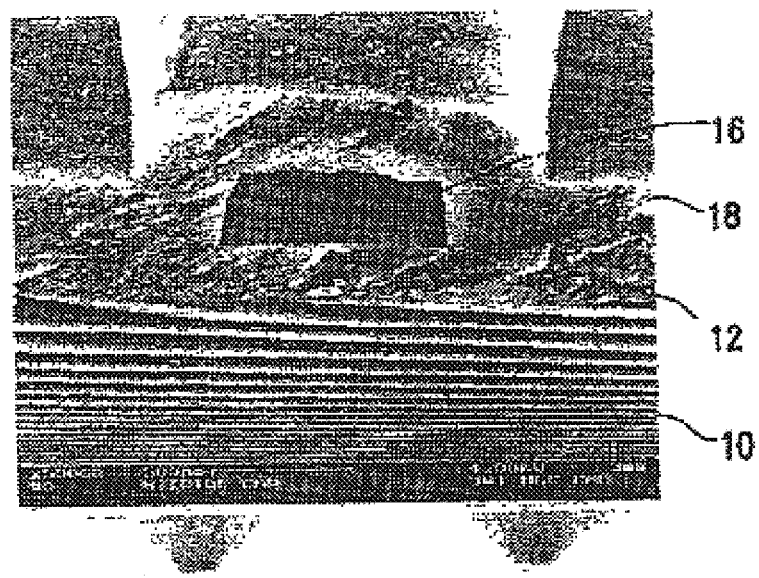
FIG. 6(b)
FIG. 6(c)
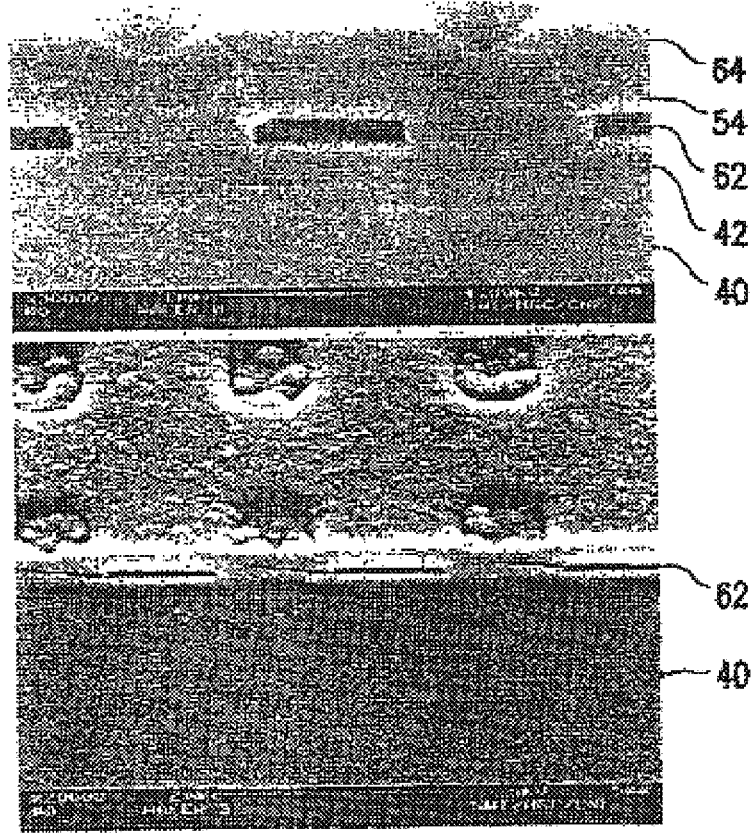

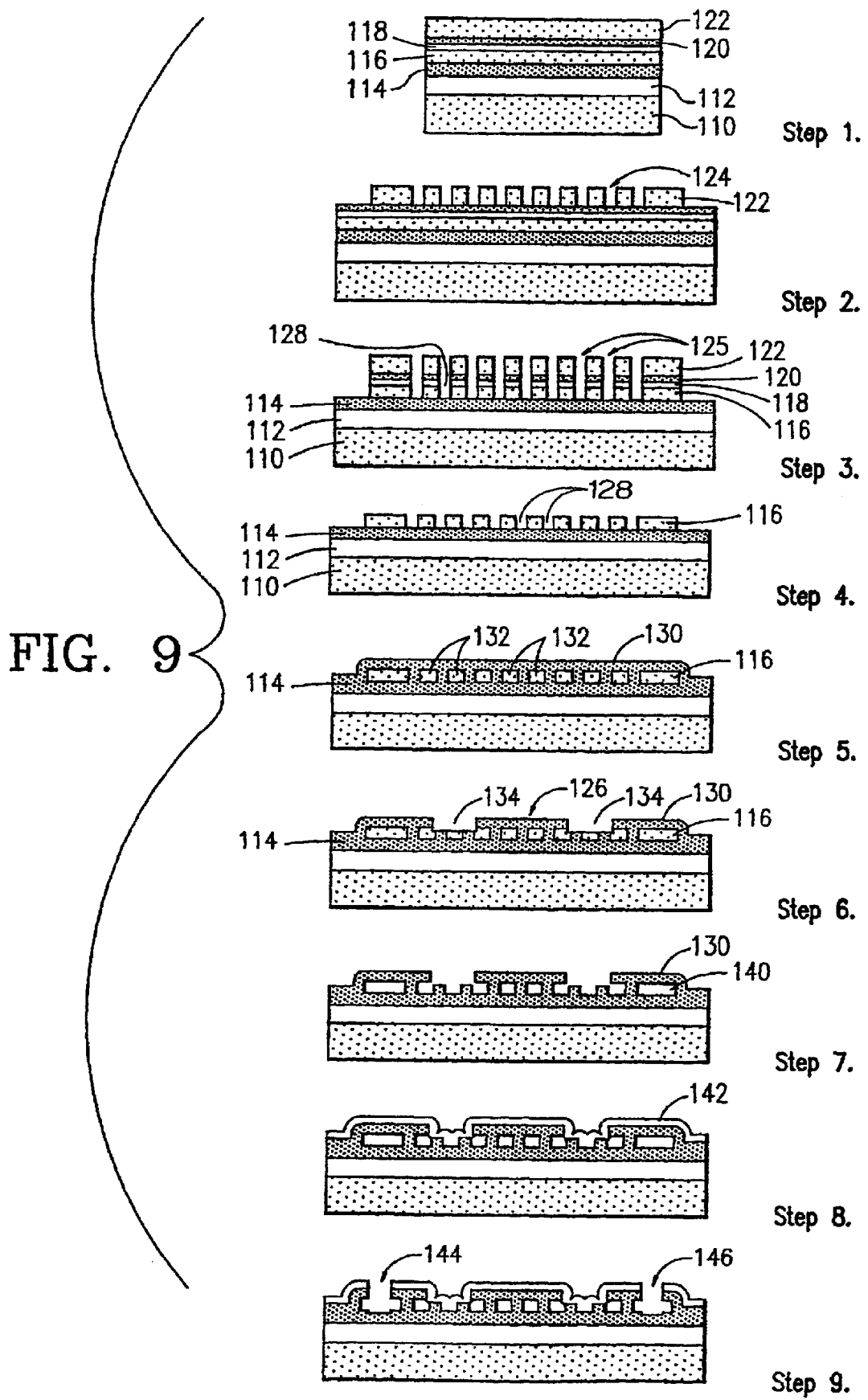

MONOLITHIC NANOFLUID SIEVING STRUCTURES FOR DNA MANIPULATION

CROSS REFERENCE TO RELATED APPLICATIONS

This application is a continuation under 35.U.S.C. 111(a) of International Patent Application No. PCT/US00/00013, filed Jan. 12, 2000, which claims the benefit of priority to Provisional Application No. 60/115,854, filed Jan. 13, 1999, and entitled "Monolithic Nanofluid Sieving Structures for DNA Manipulation", the disclosures of which are both hereby incorporated herein by reference.

The present invention was made with Government support under Grant No. R01HG01516, awarded by The National Institute of Health. The Government has certain rights in the invention.

BACKGROUND OF THE INVENTION

The present invention relates, in general, to methods of fabricating fluidic devices and to structures produced by such methods, and more particularly to processes including the removal of sacrificial layers for fabricating multi-level fluidic devices integrally with other devices on a substrate for interconnecting such devices.

The emerging field of fluidics has the potential to become one of the most important areas of new research and applications. Advances in genomics, chemistry, medical implant technology, drug discovery, and numerous other fields virtually guarantee that fluidics will have an impact that could rival the electronics revolution.

Many fluidic applications have already been developed. Flow cytometers, cell sorters, pumps, fluid switches, capillary electrophoresis systems, filters, and other structures have been developed using a variety of materials and techniques in a wide range of applications, including protein separation, electrophoresis, mass spectrometry, and others, have been developed. One of the goals of workers in this field is to develop a "total analysis system" wherein various structures are integrally formed on a single substrate, and for this purpose a variety of techniques, rag from silicon micromachining to injection molding of plastics, have been developed. All of these prior techniques, however, have in common that fluid capillaries are formed by bonding or lamination of a grooved surface to a cap layer, and in cases where multiple layers are present, these result from bonding together multiple substrates. Unfortunately, the drive to develop complex fluidic devices in the environment of a total analysis system has been hindered by the inherent difficulties with lamination-based fabrication techniques. As more devices are integrated onto a single substrate, the connection of the devices requires that connecting fluidic tubes cross over each other. With bonding technology, two capillaries cannot cross without lamination of a second wafer to the basic substrate. Further, the second wafer must be thick, resulting in large aspect ratio vertical interconnects, and ultimately resulting in a limit on miniaturization. If such devices were to reach mass production, alignment and bonding technology to handle the complex assembly would have to be developed, and whatever technology is employed would in all likelihood require costly redevelopment with each generation of smaller more complex fluidic devices.

One major application of fluidic devices is in the fabrication of artificial gel media, which has been a topic of interest for some years for scientific and practical reasons. Artificial gels differ from conventional polyalcrylamide or agarose gels currently used for DNA separation in that the sieving matrix in an artificial gel can be defined explicitly using nanofabrication, rather than relying on the random arrangement of long-chain polymers in the conventional gel. As such, the dimensions and topology of the artificial gel sieving matrix can be controlled and measured precisely. This makes it possible to test theories of DNA electrophoresis with fewer free variables. Artificial gels also have advantages over conventional gels in that conventional gels are expensive and require skilled operators to prepare them immediately before use, whereas artificial gels can be integrated with mass-produced microfabricated chemical processing chips and shipped in a ready-to-use form.

However, previous methods for fabricating artificial gels involved bonding a top layer, either glass or a pliable elastomeric material, to a silicon die with columnar obstacles micromachined into the surface. Such methods have been successful for structures with fluid gap heights as small as 100 nm, but it is difficult to establish a uniform and predictable fluid gap between a silicon floor and a glass or elastomeric top layer. An elastomer layer, and in many cases even a glass layer, can flow between the retarding obstacles in the fluid gap, either dosing the gap entirely or creating large variations in the gap height. Both methods are sensitive to particulate contamination to the extent that a single particle can render an entire device unusable.

SUMMARY OF THE INVENTION

It is, therefore, an object of the invention to provide a method for fabricating multiple fluidic devices as a monolithic unit by the use of a sacrificial layer removal process wherein fluidic devices with one or more layers can be fabricated by successive application and patterned removal of thin films. Some of these films are permanent, and some are sacrificial; that is, they will be removed before the fabrication is complete. When the sacrificial layers are removed, the empty spaces left behind create a "working gap" for the fluidic device which can be virtually any shape, and which can be configured to perform a number of different functions.

Another object of the present invention is to produce nano-fabricated flow channels having interior diameters on the order of 10 nm. Such nanometer-scale dimensions are difficult to attain with conventional micro-fluidic fabrication techniques, but the present invention facilitates fabrication at this scale while at the same time providing integration of such flow channels with other devices. These devices can provide fundamental insights into the flow of fluids in nano-constrictions and are useful in studying the behavior of biological fluids with molecular components similar in size to the cross-section of the channel. The process of the present invention permits the dimensions of the flow channels to be adjusted, for example to manipulate and analyze molecules, viruses, or cells, and the process has the potential of producing structures which will reach currently unexplored areas of physics and biology.

Another object of the invention is to provide a multi-level fluid channels fabricated on a single substrate with fluid overpasses and selective vertical interconnects between levels. Multi-level fabrication is a requirement for any complex fluid circuit, where fluid channels interconnect multiple devices on a single substrate, for without multiple levels, interconnection of large numbers of devices is either impossible or requires tortuous interconnect pathways. Lee available level of sophistication of microfluidic devices is tremendously improved by the capabilities provided by the present invention.

Briefly, the present invention is directed to procedures and techniques for overcoming the inherent difficulties and limitations of prior art laminar bonding approaches to fluidics fabrication and integration of components. In one aspect of the invention, these difficulties are avoided in the fabrication of a monolithic fluidic device by utilizing a shaped sacrificial layer which is sandwiched between permanent floor and ceiling layers, with the shape of the sacrificial layer defining a working gap. When the sacrificial layer is removed, the working gap becomes a fluid channel having the desired configuration. This approach eliminates bonding steps and allows a precise definition of the height, width and shape of interior working spaces, or fluid channels, in the structure of a fluidic device. The sacrificial layer is formed on a substrate, is shaped by a suitable lithographic process, for example, and is covered by a ceiling layer. Thereafter, the sacrificial layer is removed with a wet chemical etch, leaving behind empty spaces between the floor and ceiling layers which form working gaps which may be used as flow channels and chambers for the fluidic device. In such a device, the vertical dimension, or height, of a working gap is determined by the thickness of the sacrificial layer film, which is made with precise chemical vapor deposition (CVD) techniques, and accordingly, this dimension can be very small.

In order to provide access to the sacrificial layer contained in the structure for the etching solution which is used to remove the sacrificial layer, one or more access holes are cut through the ceiling layer, with the wet etch removing the sacrificial layer through these holes. An extremely high etch selectivity is required between the sacrificial layer and the dielectric layers in order to allow the etch to proceed in the sacrificial layer a significant distance laterally from the access holes without consuming the floor and ceiling layers which compose the finished device. One combination of materials that meets the requirements for such a process is polysilicon and silicon nitride, for the sacrificial layer and for the floor and ceiling layers, respectively. Extremely high etch selectivities can be obtained with basic solutions such as potassium hydroxide (KOH) or sodium hydroxide (NaOH), but especially with tetramethyl ammonium hydroxide (TMAH). TMAH provides an etch selectivity between silicon and silicon nitride as high as 1,500,000:1, with etch rates as high as 0.6 $\mu$m per minute. Additionally the basic solution contains no metal ions and is thus compatible with the CMOS CVD equipment used to deposit the thin film sacrificial polysilicon layer and the thin film ceiling layer.

The access holes cut in the top layer need to be covered before the device can be used. For this purpose, a sealing layer of silicon dioxide is deposited on top of the ceiling lay to fill in the access holes, and this additional thin film layer provides a good seal against leakage or evaporation of fluids in the working gap. $SiO_2$ CVD techniques which yield a low degree of film conformality, such as very low temperature oxide (VLTO) deposition, form a reliable seal without excessive loss of device area due to clogging near the access holes. If desired, the access holes may be drilled through the bottom layer, instead of or in addition to the holes in the ceiling layer, and later resealed by depositing a layer of silicon dioxide.

In one embodiment of the invention, wherein the process is utilized to fabricate artificial gels, a multiplicity of retarding obstacles in the form of vertical pillars are fabricated in a selected portion of the sacrificial layer before the ceiling layer is applied. The obstacles are defined using standard photolithographic techniques. In another embodiment of the invention, electron beam lithography is used for this purpose, permitting the fabrication of obstacles several times smaller than can be produced utilizing the photolithographic techniques.

In one example, lithography was used to define in the sacrificial layer a filter chamber incorporating an artificial gel and connected to inlet and outlet fluid channels. In this process, an array of holes was formed in a chamber region of the sacrificial layer, the holes being about 100 nm in diameter and separated by 100 nm in a square array, for example. When the ceiling layer was applied, the ceiling material filled the holes to form a multiplicity of pillars about 100 nm in diameter and separated by 100 nm. The pillars extended through the sacrificial material between the floor and ceiling layers, and when the sacrificial layer was removed the pillars formed in the chamber region the vertical obstacles of an artificial gel. The chamber region had an active area 800 $\mu$m by 500 $\mu$m, with connecting inlet and outlet flow channels, or microchannels, connected to opposite sides of the chamber to make a microfluidic device 15 mm in length. The extra length provided by the inlet and outlet capillaries was provided in the example to allow fluid interconnects to the device to be outside the footprint of an objective lens used to observe material within the filter chamber, but any desired inlet or outlet channel configurations can be used.

The interconnection of the fluid between external devices and the working gap produced by a sacrificial layer, as described above, preferably is made by way of one or more loading windows and outlet windows on the top (ceiling) surface of the inlet and outlet microchannels. These windows are defined with photolithography and are etched through the ceiling layer with RIE. They may be located at the outer ends of the microchannels, which may be near opposite edges of a silicon chip or substrate carrying the artificial gel.

In a typical use of an artificial gel device such as that described above, an aqueous buffer with fluorescent-labeled DNA molecules in solution is supplied to the loading window from a fluid reservoir which forms a meniscus with the edge of the silicon chip, and after passing through the gel the buffer is delivered to a reservoir connected to the outlet window. A potential is applied across the gel by a voltage connected across electrodes immersed in the buffer reservoirs, and the applied potential difference drives the DNA molecules through the device, where their motion is observed with epi-fluorescence microscopy.

In another aspect of the invention, multiple fluidic levels are constructed on a single substrate by repeated applications of the sacrificial layer technique. With this process, barriers between the layers can be extremely thin, because the solid sacrificial layer mechanically stabilizes the film during construction of multiple layer devices. Each layer could potentially add less than 500 nm to the thickness of the device, with miniaturization being limited only by available lithographic or electron beam techniques. The fabrication of multiple-level devices is an extension of the single-level fabrication technique outlined above. The first level is defined exactly as in the single level system, but instead of perforating the ceiling layer to provide access holes for sacrificial layer removal, holes are made in the first level ceiling layer only where there are to be connections to the second level. These vertical interconnect holes are made using the same steps used for making access perforations. If no connections are needed, then no interconnect holes are made in the first level ceiling layer. Thereafter, a second sacrificial layer is deposited over the structure, this layer having a thickness equal to the desired vertical dimension of a working gap in the second layer, and preferably being between 30 nm and 1000 nm in thickness. Photolithography or electron beam lithography is used to pattern the second sacrificial layer to define a desired structure configuration, such as fluid-carrying tubes or microchannels, fluid chambers, or the like. The second level structure may be configured to pass over fluid microchannels that were previously defined in the first-level lithography step, and the first and second level sacrificial layers may make contact with each other where vertical interconnect holes breaching the ceiling of the first level and intersecting the working gap defined by the sacrificial layer in the second level have been provided. Finally, the second level ceiling layer is deposited, in the manner previously described for a single level device, and access holes are defined as before.

If desired, additional layers may be added by depositing additional patterned sacrificial layers on prior ceiling layers in the manner described for the second level, and depositing additional corresponding ceding layers. Thereafter, the sacrificial layers are removed from all layers by a wet chemical etch, as previously described, producing a multiple-level fluidics structure. If all the layers are vertically interconnected through access holes, the sacrificial layers can all be removed together. If they are not so interconnected, the sacrificial layer is removed by way of separate access layers, which may be located at the edges of the multilevel device.

The unique approach to the fabrication of nanofluidic structures in accordance with the present invention offers several advantages over prior processes. First and foremost is the integration of fluidic devices with other devices, such as optical or electronic devices, on a single substrate, without lamination or bonding steps. Such integration can be obtained by reason of the fact that the methods of the invention rely on semiconductor manufacturing techniques and equipment already in existence in the semiconductor manufacturing industry. The ability to create multi-level structures with vertical interconnections allows significant increases in integration and functionality, allowing large-scale integration of fluidic devices and permitting fabrication of structures which allow parallel processing and high speed analysis to be performed. Since the technology is compatible with other fields of microfabrication such as planar waveguide optics and silicon-based microelectronics technology, not only can microfluidic components be integrated with each other, but they also can be integrated on a single wafer with other types of components or devices, such as those required for analysis and data collection. The fabrication techniques of the present invention permit creation of extremely small features with excellent control over dimensions and placement of devices and interconnections so that microfluidic components will be comparable in dimensions to macromolecules, facilitating the fabrication of complex biochemical analysis systems.

BRIEF DESCRIPTION OF THE DRAWINGS

The foregoing, and additional objects, features and advantages of the present invention will become apparent to those of skill in the art from the following detailed description of preferred embodiments thereof, taken in conjunction with the accompanying drawings, in which:

FIGS. 4(a) and 4(b) diagrammatically illustrate the steps used in fabricating a two dimensional artificial gel media on a wafer;

FIGS. 6A, 6B and 6C are scanning electron micrographs showing the dimensions of three different fluid gap heights in a device fabricated in accordance with FIG. 1;

FIG. 9, Steps 1–9 are diagrammatic illustrations of a second embodiment of a process for fabricating devices in accordance with the present invention;

DESCRIPTION OF PREFERRED EMBODIMENTS

The basis of the fabrication techniques of the present invention is the use of a pattern of sacrificial and permanent layers which defines the interior geometry of a fluidic device. To define the potential of the technology, several fabrication methods an applications are described herein as embodiments of the invention. A single-level, or two-dimensional embodiment of the process illustrates the basic concepts common to additional embodiments and applications, thus serving as a foundation for more complex processes and structures. Accordingly, the first embodiment of the invention will be described in terms of a process for producing a single level fluidic structure. As will be described, the process of the invention relies on techniques developed for semiconductor fabrication. For example, chemical vapor deposition (CVD) may be used to deposit the device materials, including permanent wall materials which are usually a dielectric material such as silicon nitride or silicon dioxide, and nonpermanent sacrificial layer materials, such as amorphous silicon or polysilicon. CVD is preferred, since it is ideally suited for precise control of the dimensions of a fluidic device, providing excellent precision and uniformity in the thickness of the deposited films.

Figure 1:
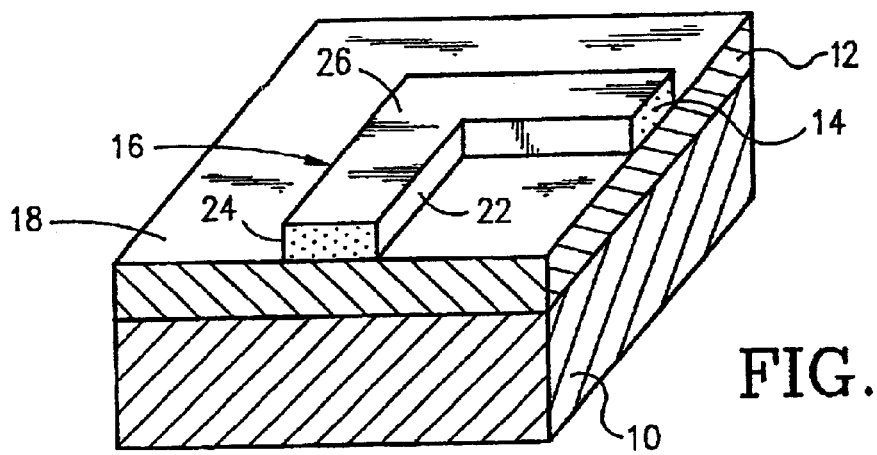
FIGS. 1–3 are partial, diagrammatic, perspective views of the process of the present invention, FIG. 1 illustrating formation of a patterned sacrificial layer on a substrate, FIG. 2 illustrating formation of a ceiling dielectric layer over the sacrificial layer, with access holes, and FIG. 3 Illustrating the steps of etching away the sacrificial layer and sealing the access holes.
Figure 2:
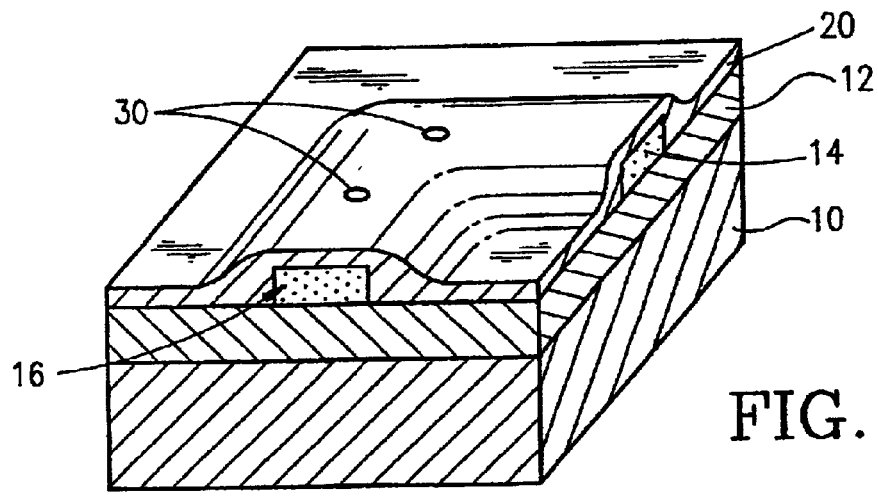
Figure 3:
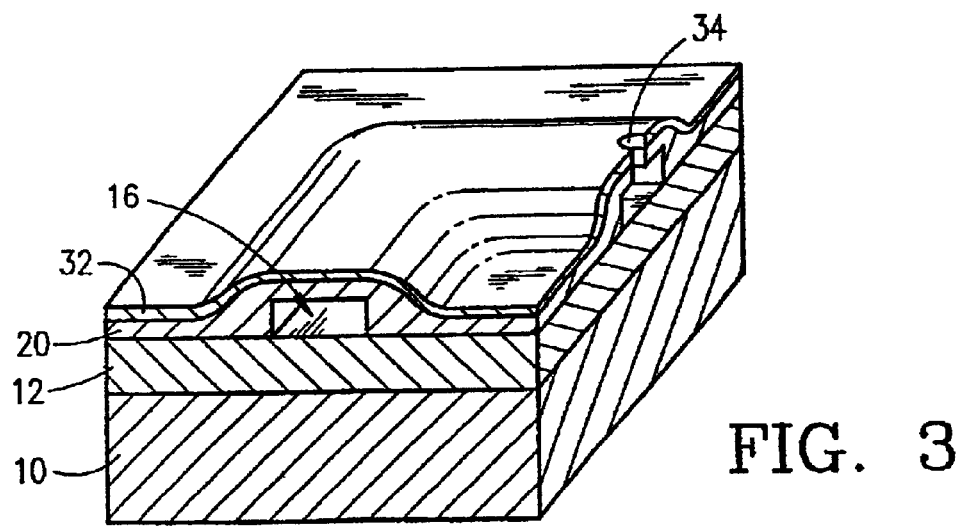

In broad outline, as illustrated in FIGS. 1, 2 and 3, the first step in the process of the present invention is to deposit on a substrate 10 a first layer 12 which will serve as the floor of the fluidic device being fabricated. The layer 12 may be a dielectric material between 30 nm and 1000 nm thick which serves as a bottom wall for the fluidic channels which are to be formed, and may be referred to as a permanent layer. A nonpermanent, or sacrificial layer 14 is deposited next, with the thickness of this thin film layer controlling the interior vertical dimensions of the final product. Films ranging from 5 nm to 10 μm may preferably be utilized for some products, but any desired thickness may be provided. The geometry of the fluidic structure that is to be fabricated, which structure may include fluid pairs, fluid chambers, sieves, filers, artificial gels or other components of the fluidic device, are then defined in the sacrificial layer 14, a suitable lithographic process, which c* include the steps of patterning a resist material, transferring the pattern to a pattern mask layer, and then transferring the pattern to layer 14, in known manner. Processes which do not use a resist material such as laser machining, may also be used to define the structures. For electron beam lithography and deep structures made with photolithography, a hard pattern mask is required to assist in pattern transfer, and silicon dioxide or aluminum hard masks may be used for this purpose, as is known in the art.

The fabrication of a fluid pathway in the form of a simple tube 16 is shown in FIGS. 1, 2 and 3. As there illustrated, after the pattern of the tube has been defined lithographically, unwanted portions of the sacrificial layer 14 are removed with reactive ion etching (RIE) to expose portions of the top surface 18 of floor layer 12. The remaining sacrificial material defines the interior shape of the tube 16, as illustrated in FIG. 1. Thereafter, a top wall layer 20 is added, covering the top surface 18 of layer 12 where it is exposed around the remaining sacrificial material 14, and covering the exposed side wall surfaces 22 and 24 and the top surface 26 of the tube 16, as illustrated in FIG. 2. This top wall layer 20 preferably is a dielectric thin film deposited by CVD techniques, and is also referred to as a permanent wall. The removal of the sacrificial layer 14 from within the now-covered tube 16 requires that a wet etch be able to get inside the tube. This can be done from the edge of the substrate if tube 16 extends to that edge, or the top layer 20 may be perforated at intervals to allow access to the interior through layer 20, as illustrated by access holes 30 in FIG. 2. An etchant such as tetramethyl ammonium hydroxide, which is used because it yields extraordinary selectivity for sacrificial layers of polysilicon or amorphous silicon over the permanent bottom wall material 12 and the permanent top wall material 20, is supplied through the ends of the tubes or through access holes 30 to remove the sacrificial layer 14. Thereafter, the ends of the tubes or the holes 30 are sealed by a layer 32 of a very low temperature oxide (VLTO) which is selected to have only moderate conformality. This material is desirable because it deposits as little oxide as possible on the interior walls of tube 16 while still closing off the access holes 30. Once the device is sealed, standard lithography and etching techniques are used to open loading holes, such as aperture 34, through the top layer 20 and the sealing layer 32 into tube 16 in appropriate places to enable the interior of the tube 16 to interface with an external fluid interconnect device. The fluid pathways and chambers produced by the removal of the sacrificial layer 14 and exemplified by tube 16, may be generally referred to herein as the "working gap", or "fluid gap" of the fluidic device.

Figure 4A:
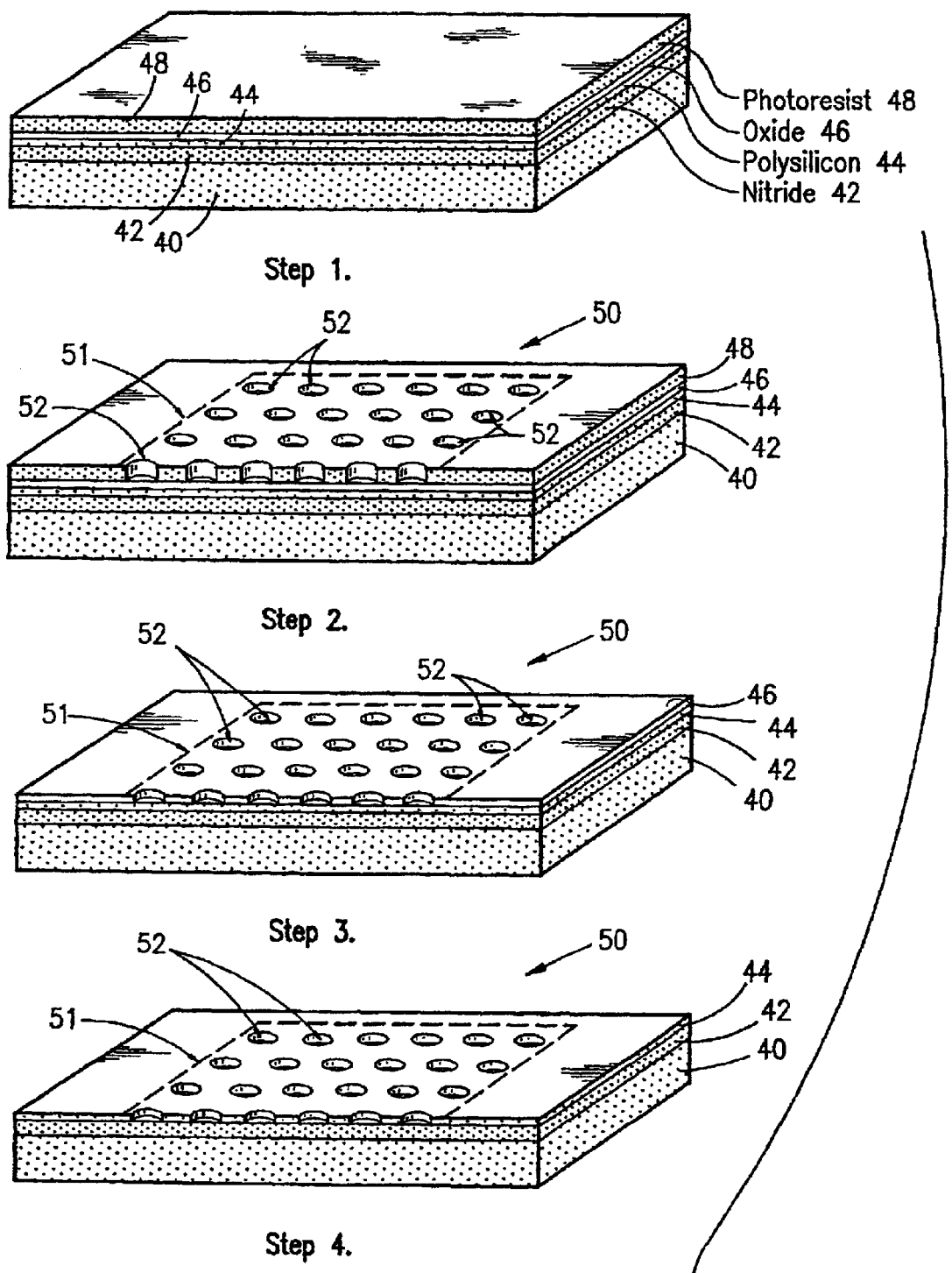

The basic process steps of the invention are outlined in greater detail in a partial, schematic, perspective view in FIGS. 4(a) and 4(b) as including process steps 1–8. A three-inch (100) N-type silicon wafer 40 was used as a substrate in this process. The silicon wafer served only as a carrier for the thin-film fluidic device, and any material compatible with a CMOS film deposition furnace could be used as a substrate. The wafer was subjected to a conventional RCA cleaning step, and covered with a first, 420 nm thick bottom thin film layer 42 of low pressure CVD (LPCVD) silicon nitride. Immediately following this, a polysilicon sacrificial layer 44 was grown over the silicon nitride layer 40, the thickness of the polysilicon layer serving to establish the height of the fluid gap in the final device. To investigate the behavior of the process with different fluid gap heights, three wafers with different polysilicon sacrificial layer 44 thicknesses were fabricated: 120 nm, 280 nm and 530 nm. In each case, following polysilicon deposition, a thermal oxide hard mask 46 was grown on the surface. The choice of thickness for the hard mask was made according to the thickness of the polysilicon layer. For the thinnest polysilicon layer, a mask layer of approximately 10 nm of $SiO_2$ was used. For the dicker polysilicon films, an 80 nm thick mask layer 46 was applied. A photoresist layer 48 was then applied to the top surface of layer 46.

A pattern 50 for a fluidic device having inlet and outlet tubes, or microchannels, (not shown) connected to a fluid chamber 51 (indicated by dotted lines) defines in the resist layer 48 (Step 2) an array 52 of retarding obstacles such as those that might be fabricated as an artificial gel or a sieve. The pattern 50 is produced using standard photolithographic techniques. In one example, the pattern 50 for the array 52 of retarding obstacles included a multiplicity of 1.0 μm diameter cylindrical holes whose centers were separated by 2.0 μm. The pattern of holes was transferred from the resist layer 48 to the oxide hard mask layer 46 with a $CHF_3/O_2$ RIE, and subsequently was transferred into the polysilicon layer 44 (Step 3) using a three-step $Cl_2/BCl_3$ RIE. The holes making up the array 52 in the sacrificial layer were the template in which the obstructing pillars were later formed.

In step 4, the wafer was again subjected to an RCA clean, followed by a final dip in 10:1 solution of 48% hydrofluoric acid and DI water for 30 seconds to remove the oxide hard mask 46 from the polysilicon surface. The wafer was rinsed, spin-dried and coated with an additional 420 nm thick layer 54 of LPCVD silicon nitride (Step 5). Since LPCVD silicon nitride coats conformably, it coated the floor and walls of the holes of array 52 cut in the polysilicon layer 44, thus forming obstructing pillars 56 in those holes. These pillars extend substantially the full thickness of layer 44 and contact the top surface of bottom wall 42.

Irrigation holes 60 were then defined in the top nitride layer 54 (Step 6) using photolithography aligned to the previous layer. A photoresist pattern (not shown) masked a $CF_4$ RIE, which cut all the way through the silicon nitride top, or ceiling layer 54, exposing the polysilicon layer 44 underneath. The photoresist was removed by immersion in acetone, followed by a 10 minute $O_2$ plasma strip. Native oxide which formed during the oxygen plasma strip was removed with a 20 second dip in hydrofluoric acid buffered 30:1 with ammonium fluoride.

The sacrificial layer 44 was then removed with a 5% solution of TMAH in water heated to 80° C. The irrigation holes 60 were conservatively placed 20 microns from each other. After 40 minutes of immersion in the hot TMAH, the polysilicon layer 44 was completely removed (Step 7), leaving a working gap 62 between the bottom wall 42 and the top wall 54. No degradation of the silicon nitride layers 42 or 54 was detected.

The wafer was again RCA cleaned and coated with a layer 64 of very low temperature oxide (VLTO) to seal the irrigation holes 62. For a structure with a working gap of 500 nm, a 1000 nm thick film sealing layer 64 of oxide was deposited. For thinner structures, a 500 nm film 64 was sufficient to seal the irrigation holes 60. Leaks in the structures were readily detected by immersing the sealed wafer in water or some other solvent. If a fluid channel contained a leak, it rapidly filled with liquid and a striking change in color was observed. One wafer was soaked for 24 hours, and although some slow leaks were found, over 90% of the structures fabricated on the wafer remained dry.

The three wafers mentioned above e were coated with a protective layer of photoresist and scribed with an automated diamond scriber through the centers of a row of pillars 56 and through an irrigation hole 60, as illustrated in the sectional views of Steps 1–8 in FIG. 4. The photoresist was removed by spin-rinsing with isopropanol, acetone and isopropanol again. The wafers were cleaved, leaving the working gap 62 and cross-sections of pillars 56 open to the outside at two edges of each chip. The cleaved chips were annealed at 900 C for 40 minutes with dry oxygen flow to grow an insulating layer 66 (FIG. 5A) of thermal $SiO_2$ on the freshly cleaved edges.

Figure 5A:
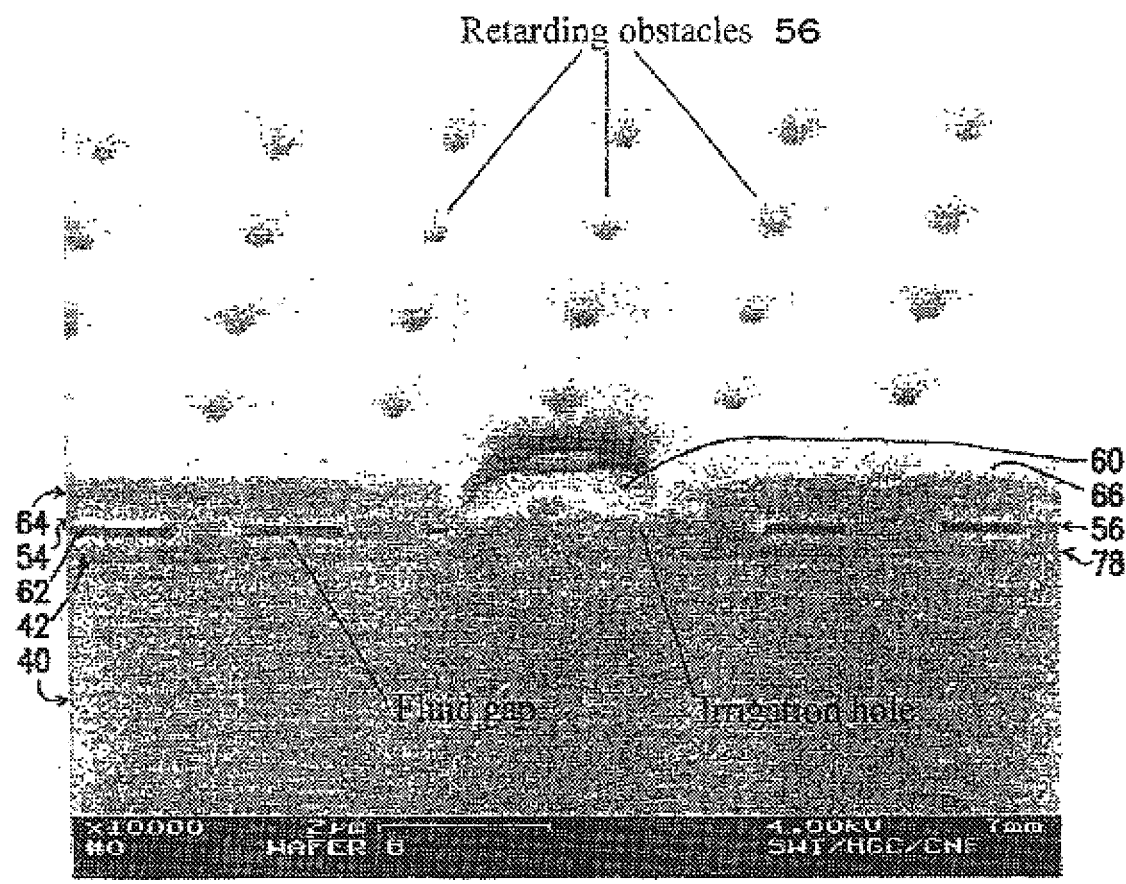
FIG. 5A is a scanning electron micrograph of an irrigation hole formed in the media of FIG. 1, after resealing by a VLTO oxide, the wafer having been cleaved the center of the irrigation hole to provide a cross-sectional view.

The finished devices were inspected with white-light interferometry and scanning electron microscopy (SEM). FIG. 5A is a scanning election micrograph of a portion of a wafer, illustrating the working gap 62, pillars 56, and irrigation hole 60 filled with oxide 64 in a working chamber 51 for use as an artificial gel. No variation could be detected in the height of the working gap between the two nitride layers. There was some polysilicon film loss associated with the growth and removal of the oxide hard-mask, so the final devices had fluid gap heights of 63 nm, 266 nm (illustrated in FIG. 5A), and 497 nm. There was some sagging of the top nitride layer at the cleaved edges which took place during the 900° C. anneal step.

Figure 5B:
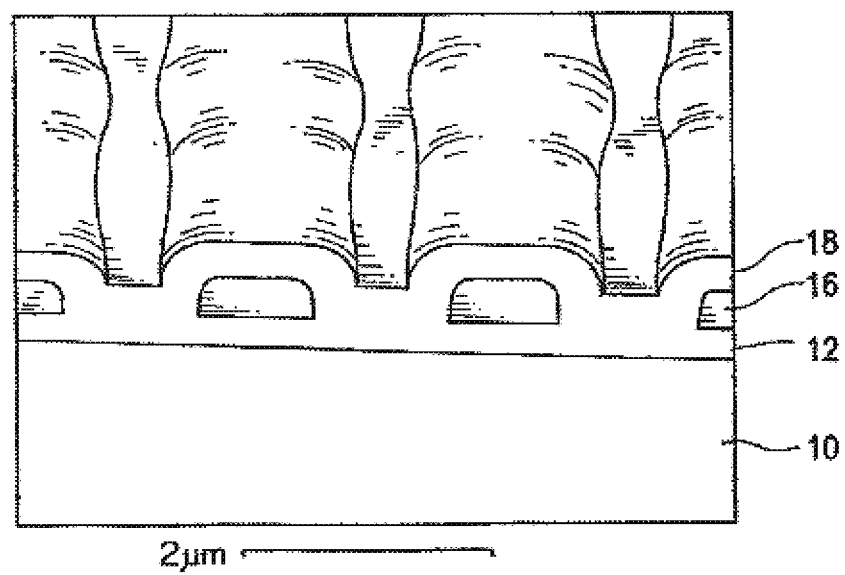
FIG. 5B is a scanning electron micrograph of a cleaved edge of a device fabricated in accordance with FIG. 1, showing micron-sized tubes, or microchannels, buried beneath a silicon nitride layer.

FIG. 5B is a scanning electron micrograph of a cleaved edge of a wafer, illustrating a plurality of micron-sized tubes, or microchannels, such as the tube 16 of FIG. 3. FIGS. 6A, 6B and 6C are scanning electron micrographs showing the dimensions of the working gaps for the three wafers discussed above. FIG. 6A is a micrograph of a wafer having a fluid tube 16 with a working gap height of 497 nm, and without a VLTO sealing layer. FIG. 6B is an enlarged micrograph of the cleaved edge of a working gap chamber of FIG. 5A, having a working gap 62 with a height of 266 nm, and including a VLTO sealing layer 64. FIG. 6C is a micrograph of a cleaved edge of a working gap chamber, having a gap 62 height of 63 nm.

Figures 7A, 7B:
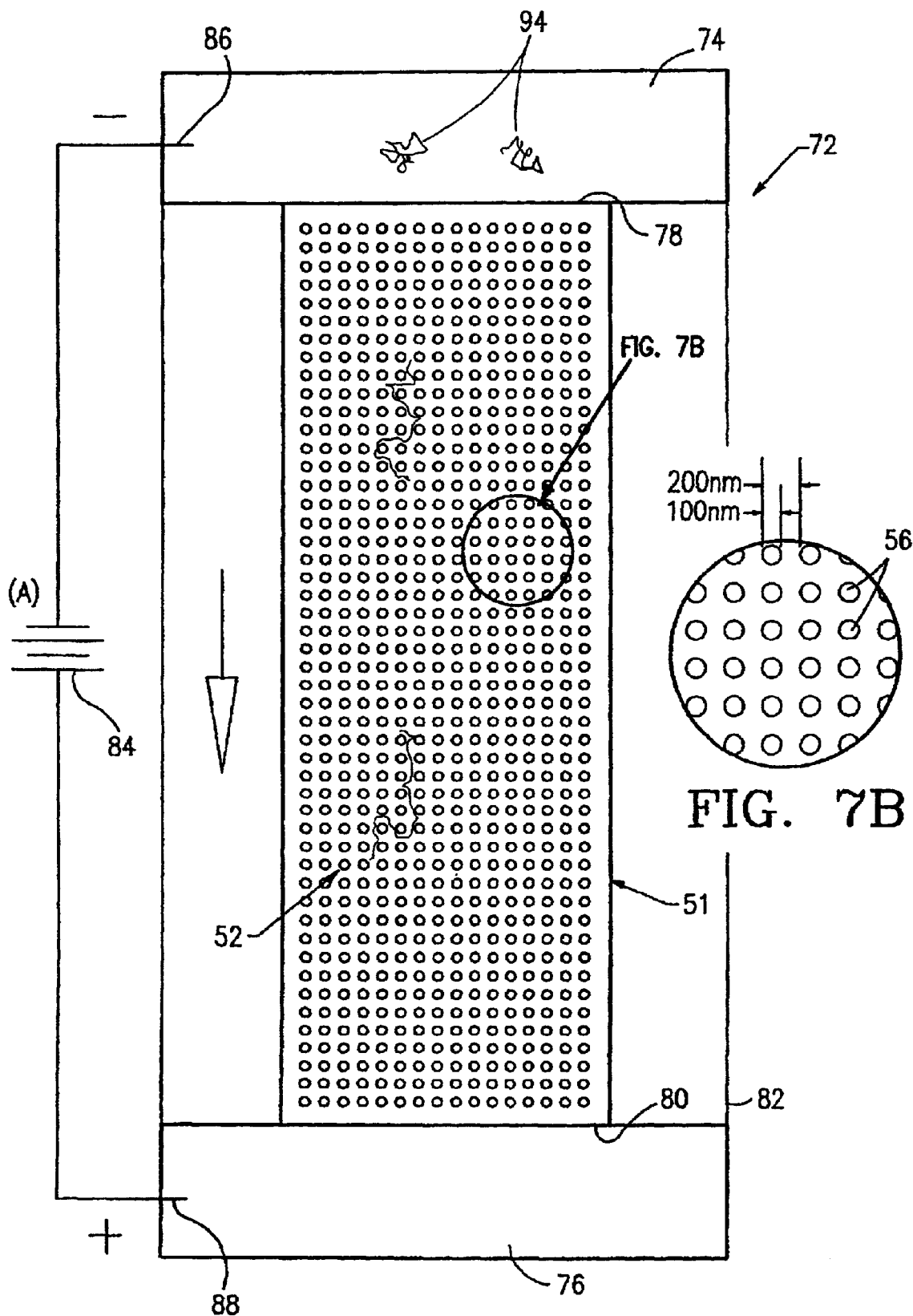
FIG. 7 is a schematic diagram illustrating the operating principle of a sieving structure fabricated in accordance with the present invention.

To test the operation of an artificial gel chamber 51 fabricated by the foregoing process, a Plexiglas jig 72 was fabricated (see FIGS. 7A and 7B) which allowed the meniscuses of two overfilled buffer reservoirs 74 and 76 to make contact with the cleaved exposed edges 78 and 80, respectively, of the chamber, and thus with the device's fluid gap (62 in FIG. 4). A silicon chip 82 cleaved from a wafer and bearing the chamber 51 was affixed to the jig 72 with vacuum grease. A voltage source 84 was connected across platinum electrodes 86 and 88, which were immersed in the buffer reservoirs 74 and 76, respectively, for driving a current through the chamber 51. The FIG. 72 and artificial gel chamber 51 were mounted on the stage of an upright fluorescence microscope. As illustrated, the artificial gel chamber 51 was a thin flat channel fabricated on the chip 82 in the form of a working gap, or fluid gap such as the gap 62, in which was located an array 52 of vertical submicron pillars, or obstructions 56 such as those described with respect to FIG. 4, and illustrated in the enlarged partial view of FIG. 7B.

λ-phage DNA was stained with YOYO-1 (Molecular Probes) to 1 dye molecule (illustrated at 94) per 10 base pairs, and was diluted to 0.5 μg/ml DNA in 0.5× tri-borate EDTA (TBE) buffer with 3% mercaptoethanol added to prevent photobleaching. The solution including molecules 94 was injected in the cathode reservoir 74 of the sample jig 72, and voltages ranging from 0–20 V were applied across the 5 mm-long chamber 51. DNA molecules 94 were observed to move electrophoretically through the artificial gel obstructions 56 in all three fluid gap heights, although in the smallest fluid gap height (63 nm) structures, the channel had an enhanced population of shorter molecules.

Figure 8A:
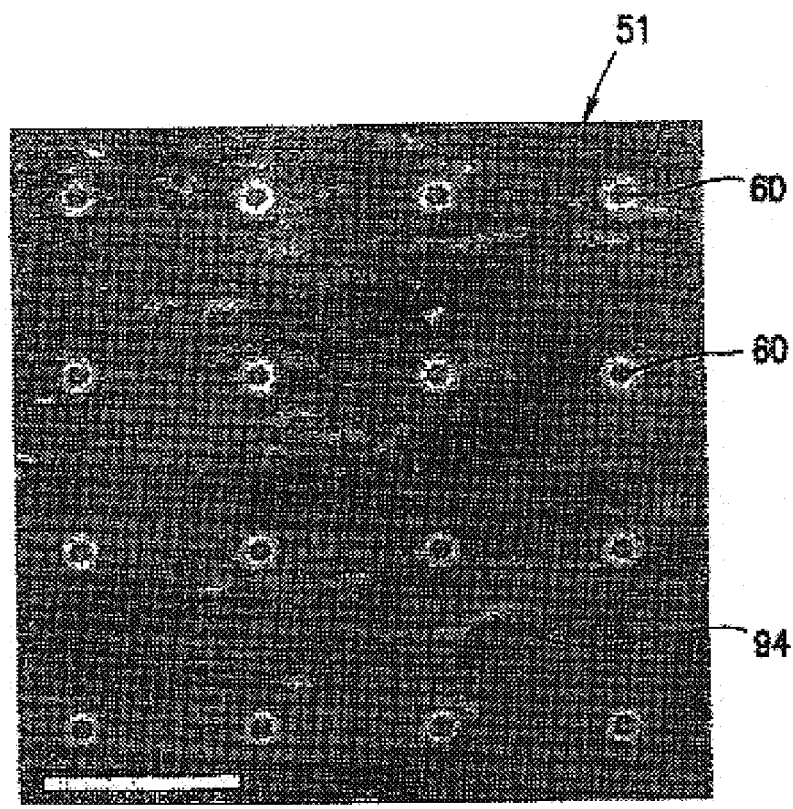
FIGS. 8A and 8B are fluorescence optical micrographs showing DNA molecules in an artificial gel fabricated in accordance with the present invention.
Figure 8B:
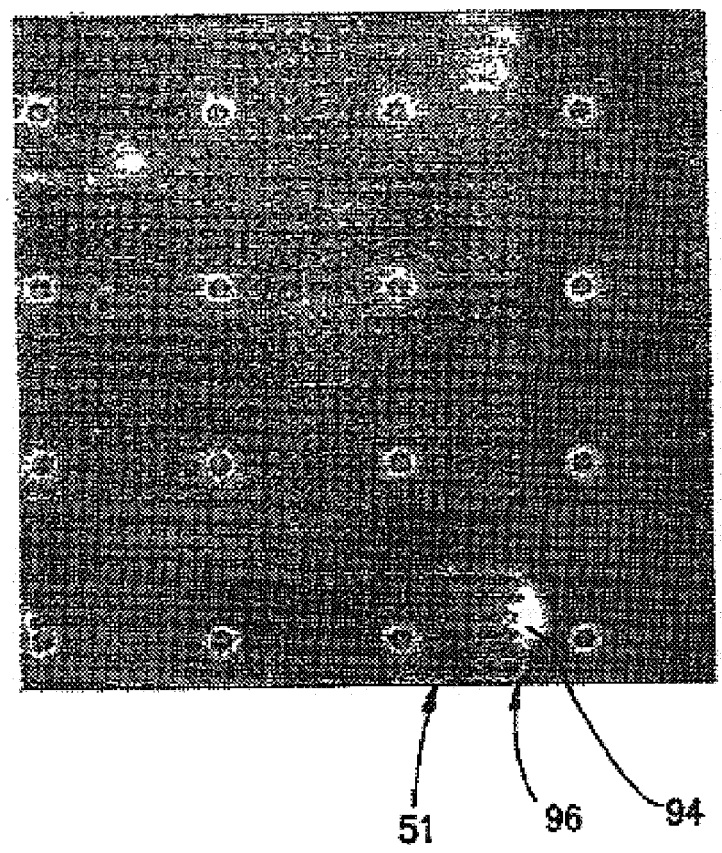

The motion of the DNA was observed in chamber 51 with a 100×0.9 NA air immersion objective. Fluorescence was excited with a 50 W merry arc lamp with an excitation filter cutoff at 490 nm. FIG. 8A shows a fluorescence micrograph of DNA molecules 94 moving through the chamber 51 with an applied potential of 5 V. This region is free of closely-spaced obstructions, so the DNA molecules are moving freely under the influence of the electric field. The image was accumulated over a 10-second interval, so the horizontal streaks in the picture represent the trajectories of the DNA molecules as they move from right to left in the frame. The highlighted circles are the sealed access apertures 60. FIG. 8B shows a portion of the boundary between chamber 51 with densely spaced retarding obstacles 56 and a region of the assembly 72 prior to the obstacles. In this image, some molecules have become trapped at the threshold 96 of the obstructed region, while others proceed.

The process steps for a second embodiment of the fabrication process of the invention, utilizing electron beam lithography, are outlined schematically in FIG. 9. Three-inch (100) N-type silicon wafers, indicated at 110 in Step 1 of FIG. 9, were used as a substrate in this process. The silicon wafers served only as carriers for the thin-film devices; any material compatible with CMOS film deposition furnaces could be used as a substrate. The wafers were subjected to an RCA clean and a 1.0 $\mu$m thick film 112 of a permanent wall material such as a thermal silicon dioxide was grown in the surface. After oxidation, a 190 nm thick permanent film 114 of low-stress LPCVD silicon nitride was deposited, followed by a nonpermanent sacrificial layer 116 formed as a 500 nm thick film of LPCVD polysilicon. A 100 $\mu$m thick hard mask layer 118 was thermally grown in the polysilicon layer 116, and a 40 nm thick film 120 of aluminum was thermally evaporated over the oxide hard mask to assist in pattern transfer and provide a conductive substrate for electron beam lithography (EBL). Finally, a 200 nm thick film 122 of 496 K PMMA resist material was spin coated over the aluminum and baked for 10 minutes at 170° C. on a vacuum hotplate.

Figure 10:
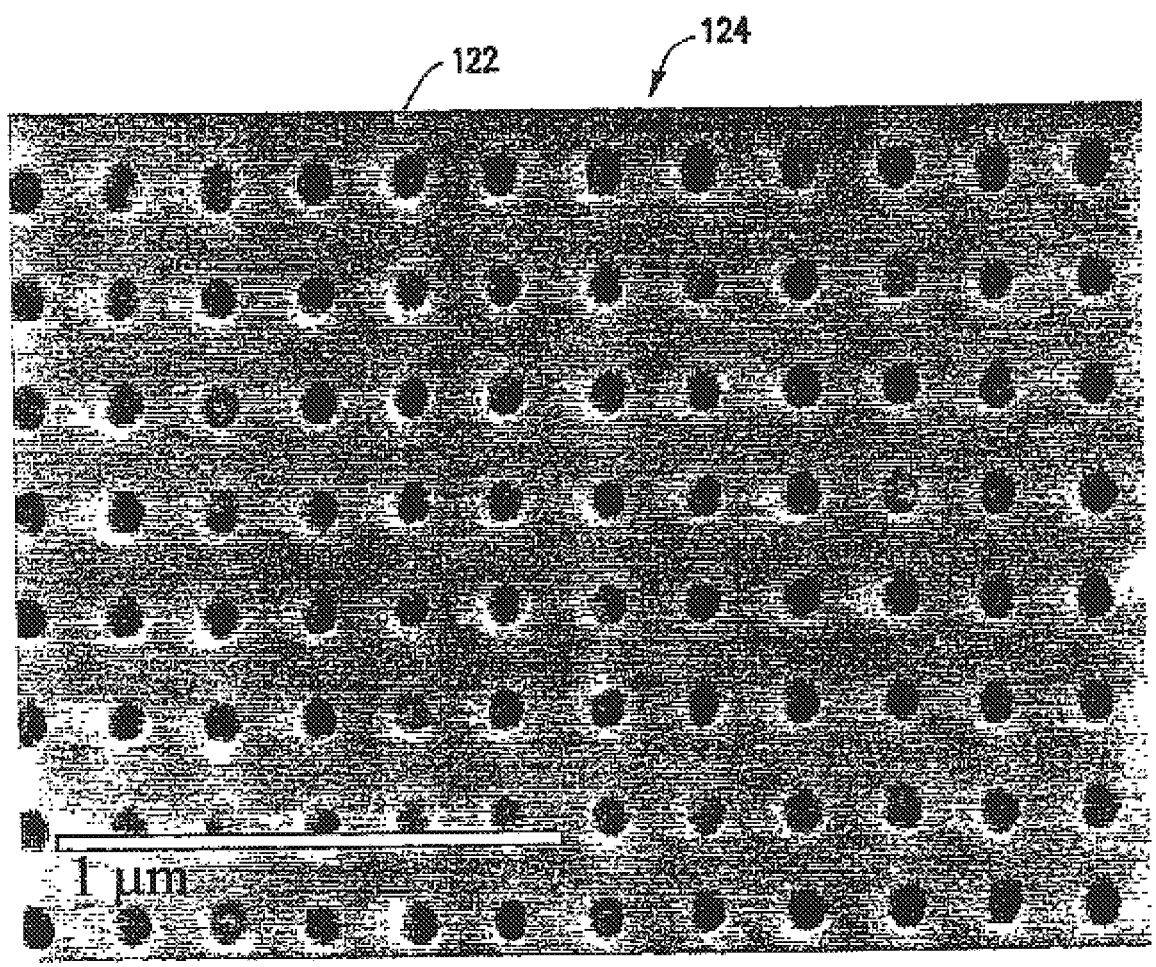
FIG. 10 is a scanning electron micrograph of a resist layer after electron beam patterning and development in accordance with the embodiment of FIG. 9, Step 2.

To pattern the resist layer 122, electron beam lithography was carried out (Step 2) to form a mask pattern 124, using a Leica-Cambridge 10.5 at 1.0 nA and a spot size of 70 nm for the fine features, and 40 nA for the coarse features. The dot dose was 18 fC. To avoid shape overhead processing time, the dots were written "on-the-fly" without beam blanking between dots. For these exposure times, the beam shift and settling time are fast enough that there are no artifacts in the dot shape from the beam movements. The resist 122 was developed for 1.5 minutes in 1:1 MIBK:IPA, rinsed in IPA and blown dry with filtered dry nitrogen. FIG. 10 is a scanning electron micrograph which shows the resist pattern 124 in a dense pillar region after it has been patterned and developed.

Figure 11:
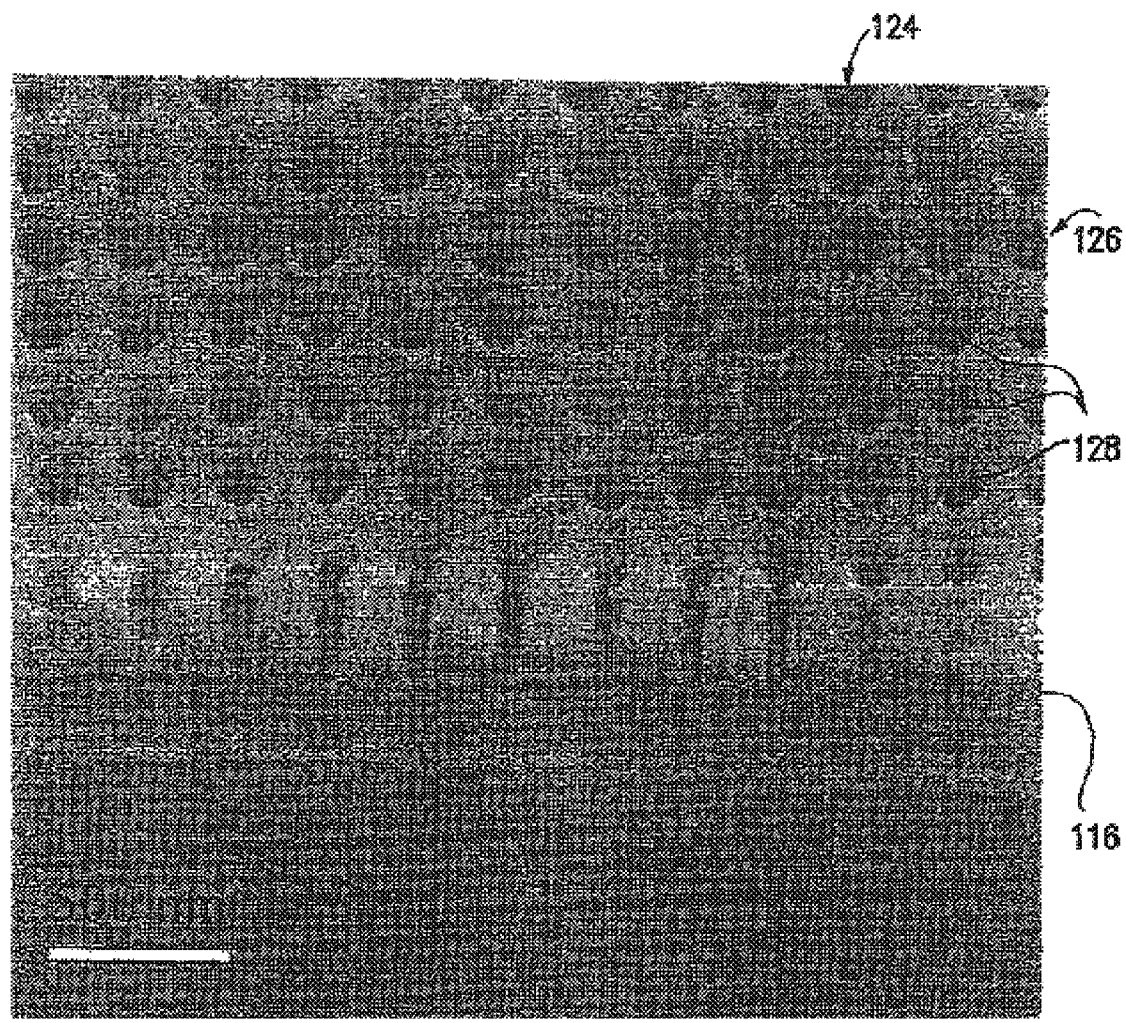
FIG. 11 is a scanning electron micrograph of a device fabricated in accordance with the process of FIG. 9, step 3, after transferring a pattern of holes utilizing dry etching.

The resist pattern 124 was transferred to the aluminum layer 120 (Step 3) with a chlorine ($Cl_2$) boron trichloride ($BCl_3$) and methane ($CH_4$) reactive ion etch (RIE). The aluminum mask was then used to pattern the $SiO_2$ hard mask layer 118 with a $CF_4$ etch Finally, the $SiO_2$ hard mask was used to pattern the polysilicon sacrificial layer 116 with a three-step $RIE^{12}$ with $Cl_2$, $BCl_3$ and $H_2$. At this point, the sacrificial layer 116 was fully patterned with a dense array 125 of obstructions in an active area 126 (such as the chamber 51 previously described) of the device (FIG. 11), as well as with the channels required to bring fluid to the active area of the device. FIG. 11 is a scanning electron micrograph showing the sacrificial layer 116 after the RIE transfer of pattern 124 is complete. The isolated holes 128 in the sacrificial layer will later become isolated obstructions in the gap after the top layer is deposited and the sacrificial layer removed, as was described above with respect to the first embodiment.

The sample was again RCA-cleaned and dipped in a 1:10 dilution of hydrofluoric acid in deionized water for 20 seconds to remove the $SiO_2$ hard mask layer 118 (Step 4). The wafer was rinsed and spin-dried and the sacrificial layer was covered by a permanent top wall material such as a layer 130 of 320 nm thick low-stress LPCVD silicon nitride (Step 5). The top wall material 130 is selected to be extremely conformal, so in addition to coating the top surface of layer 116, it also coats the sidewalls and floor of each of the holes 128 etched in the sacrificial layer 116. This deposition creates columns, or pillars 132 of silicon nitride or other top wall material buried in the sacrificial layer 116 By regulating the thickness of layer 116 and the diameter of the holes 128, each column may have an aspect ratio (height to width) of about 5:1. To remove the sacrificial layer 116, access holes 134 were photolithographically defined in a Shipley 1813 positive photoresist layer (not shown) deposited on the top wall layer 130, using a 5× g-line reduction stepper and standard exposure conditions. The access holes were 2 $\mu$m in diameter, in a square array with a 20 $\mu$m period. The resist was developed in 1:1 Shipley MF312:deionized water for 1 minute. The access holes 134 were transferred to the silicon nitride top layer 130 (Step 6) with a $CF_4$ RIE. The photoresist layer was stripped in Shipley 1165 photoresist remover. The wafer was subjected to an $O_2$ plasma strip to remove any residual photoresist.

Figure 12A:
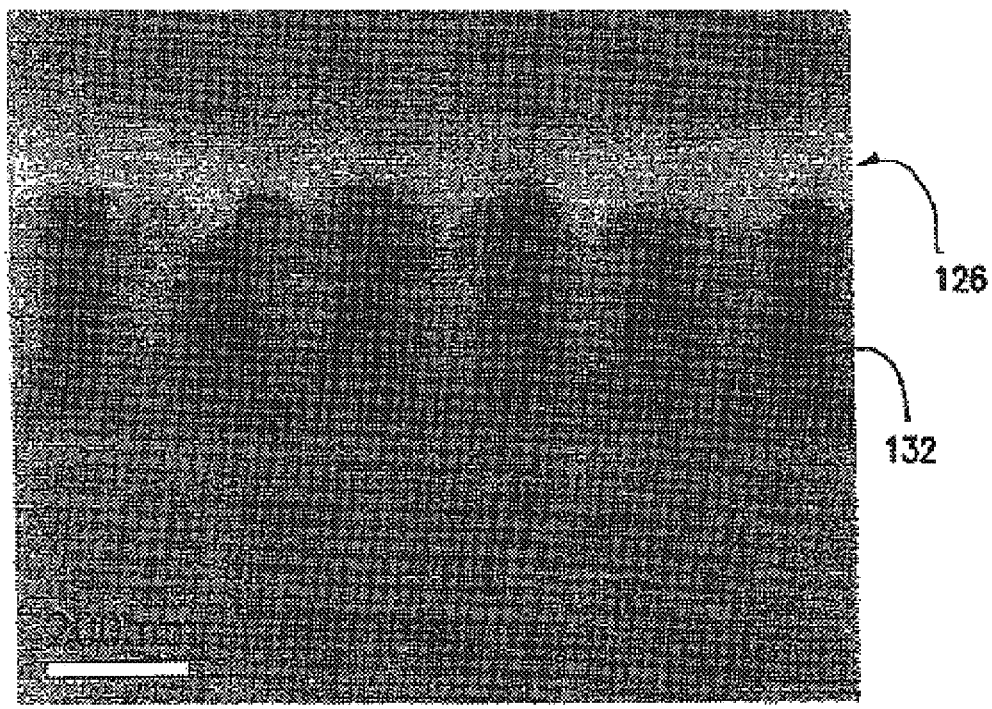
FIGS. 12A and 12B are scanning electron micrographs of the device of FIG. 9, Step 7, taken at 45° after removal of the sacrificial layers, FIGS. 12A and 12B showing the same structure at two different magnifications.
Figure 12B:
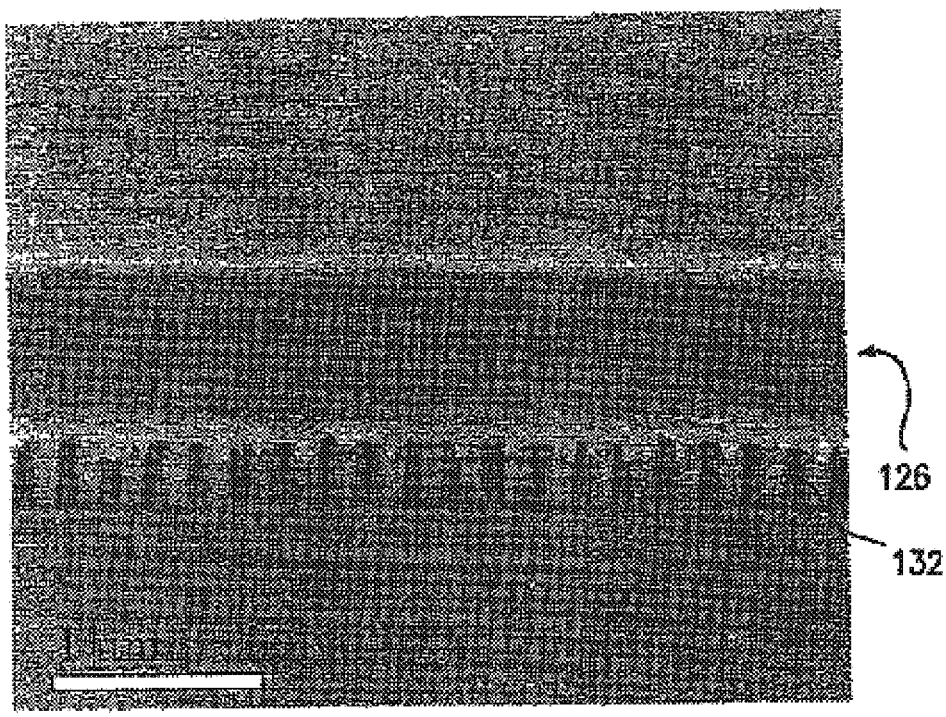

Prior to the removal of sacrificial layer 130, the wafer was dipped in hydrofluoric acid buffered 6:1 with ammonium fluoride to remove any native oxide which may have formed during the $O_2$ plasma strip. The sacrificial layer removal (Step 7) was performed with a 5% TMAH solution in water maintained at 75 C with a temperature-controlled hot-plate. For both cost and convenience, the TMAH solution used was actually a photoresist developer, Shipley MF312. In 40 minutes the sacrificial layer removal was complete, leaving a working gap 140 in place of the sacrificial layer between top and bottom walls 130 and 114. The devices were rinsed in running deionized water for an hour and blown dry with filtered dry nitrogen. FIGS. 12A and 12B are scanning, electron micrographs taken at a 45° angle&and at different magnifications, showing the dense array of pillars 132 in active region 126 of the device after the sacrificial layer removal. The pillars 132 are obstructions in the fluid flow path through the active area 126 of the artificial gel, or filter, and have vertical sidewalls and uniform size and separation The uniformity of the pillar height at this stage is better than 5 nm over the device.

Figure 12C:
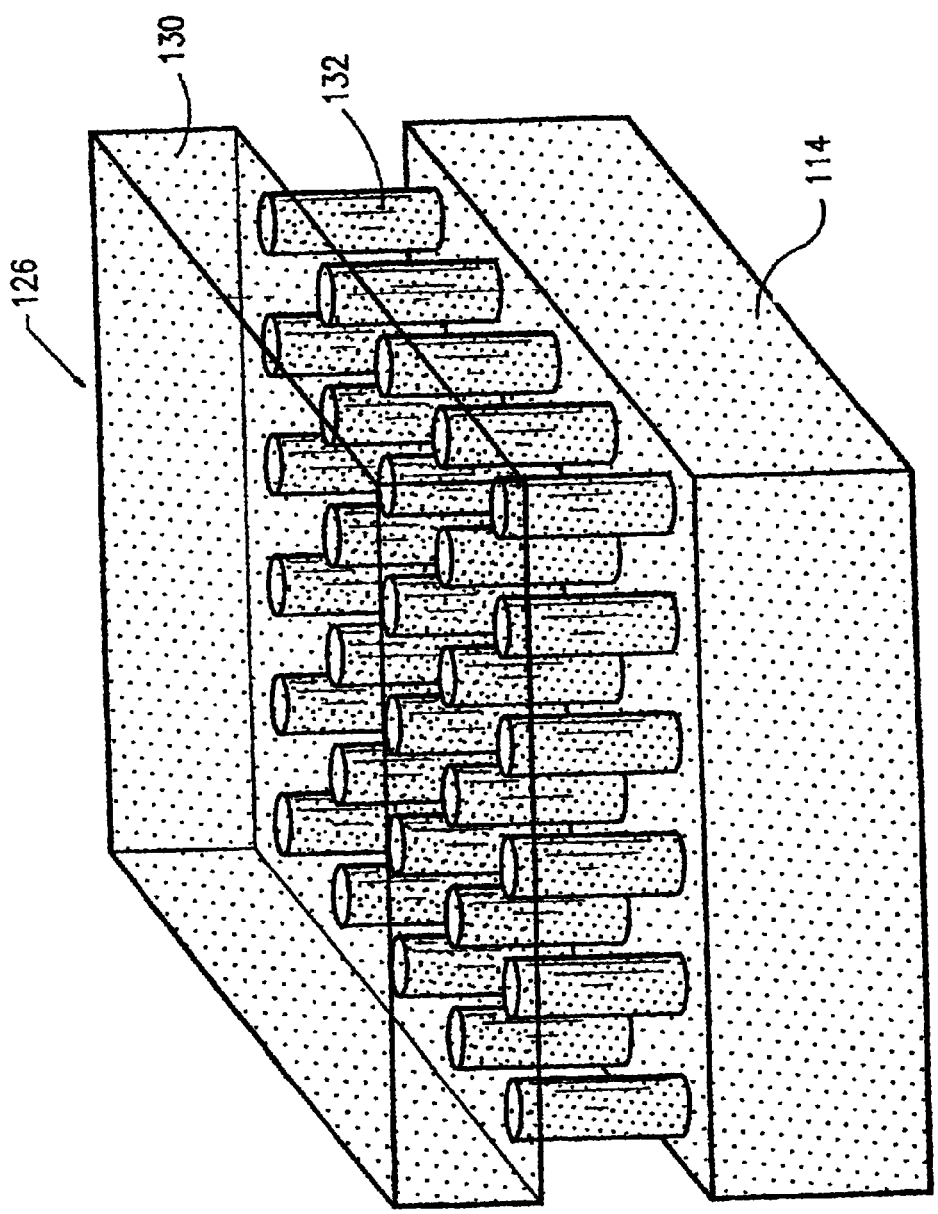
FIG. 12C is a diagrammatic illustration of a working gap containing closely-spaced pillars.

FIG. 12C is a diagrammatic illustration of the active area 126 of the working gap, showing closely spaced vertical pillars 132 extending through fluid or working gap 140 between a lower floor layer 114 and a ceiling layer 130. Since the layers 114 and 130 preferably are optically transparent, the movement of molecules or particles through the working gap 140 and between the obstacles, or pillars, 132 can be monitored and measured optically, as will be described.

To seal the access holes, a 2.5 $\mu$m film of VLTO oxide 142 was grown over the silicon nitride top layer 130 (Step 8). The devices were checked for leaks by immersion in DI $H_2O$. When a device is not fully sealed, it rapidly fills due to capillary forces. This is readily seen even with the naked eye, because the thin film stack changes color when the gap fills with water. The devices were found to have sealed without any leakage.

Figure 13:
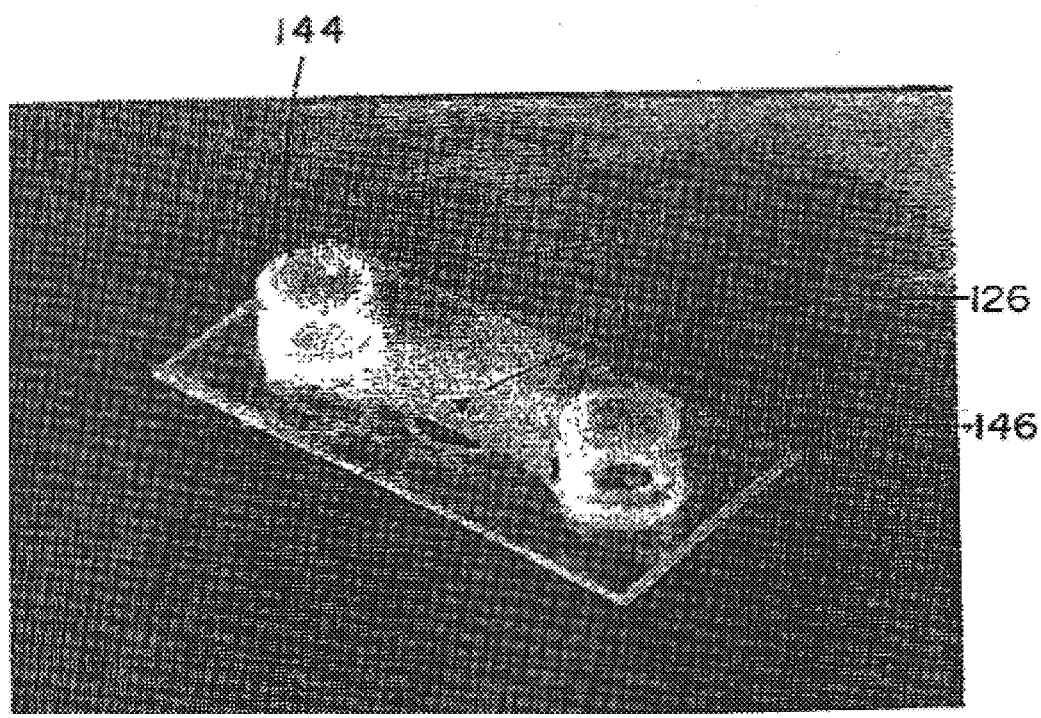
FIG. 13 is a photomicrograph of a completed wafer, illustrating loading and exit windows at opposite ends of the wafer.

To test the operation of an artificial gel fabricated n accordance with the foregoing process, photolithography was used to define loading windows 144 and 146 at the ends of the device (Step 9) as illustrated in the scanning electron micrograph of FIG. 13. A 5 $\mu$m thick layer of Shipley 1045 resist was patterned with a g-line 5× reduction stepper. The resist was developed for 4 minutes in Shipley MF312 diluted 1:1 with deionized water. The loading windows 144 and 146 were etched most of the way through the 2.5 $\mu$m thick film 142 of VLTO with a magnetron induction etch (MIE) using $CHF_3$ as the etch gas. The wafer was then scribed for later cleavage with the photoresist still in place. The etching of the windows 144 and 146 was completed with a much slower $CHF_3$ RIE. The resist was removed with acetone and isopropanol on a photoresist spinner.

Figure 14:
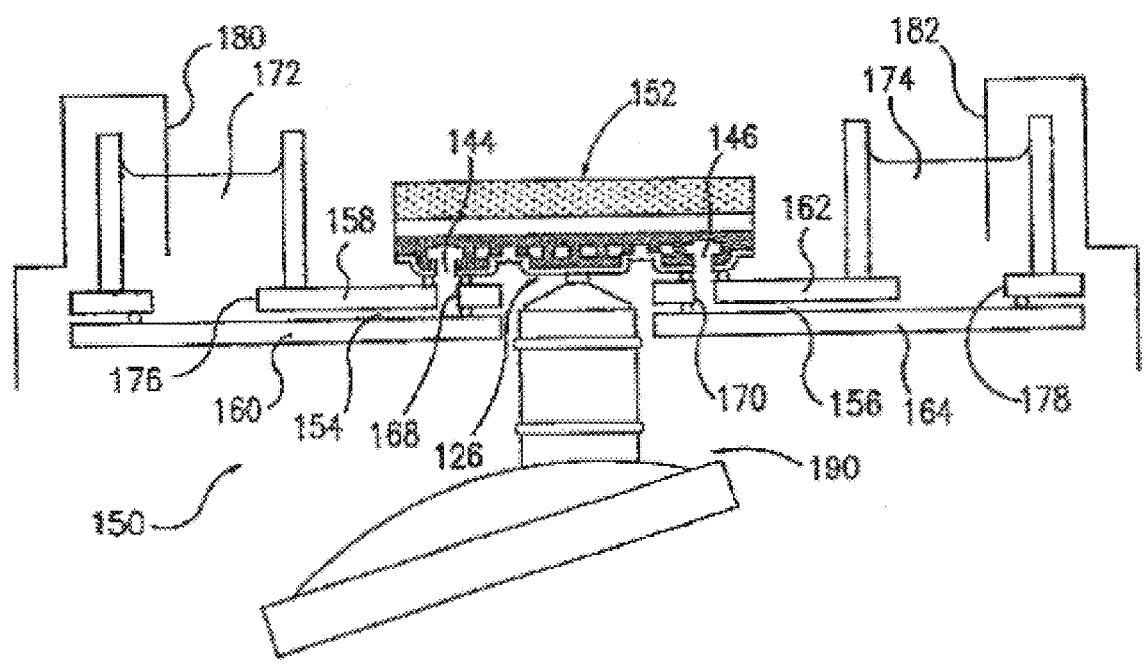
FIG. 14 diagrammatically illustrates a fluid interconnection structure for supplying fluids to devices fabricated in accordance with the present invention.

Fluid interconnects were established with the front face of the device in locations which would not interfere with the microscope objective used to observe the motion of molecules through the active region 126, where the obstructions are closely spaced to provide an artificial gel configuration. A separate interconnect "package" was manufactured for each device and permanently bonded to it. Such a package is generally indicated at 150 in FIG. 14 as being connected to a wafer 152 carrying an active region 126. Fluid channels 154 and 156 were defined between two 24×50 mm No. 1 cover slips 158, 160, and 162, 164, respectively, using silicone RTV. The channels 154 and 156 were connected to corresponding loading windows 144 and 146, respectively, through holes 168 and 170 machined in coverslips 158 and 162. The fluid channels 154 and 156 were connected to corresponding 1 cm diameter Pyrex reservoirs 172 and 174 that were bonded with RTV over corresponding holes 176 and 178 in the top cover-slips 158 and 162. The reservoirs contained gold electrodes 180, 182 connected across a voltage source (not shown) to drive a current through the device. The reservoirs also served as receptacles for loading the solution which contains material to be passed through the region 126. The motion of molecules or the like through region 126 was observed by fluorescence microscopy, using, for example, an optical microscope having a 100×, 1.4 N.A. oil immersion objective lens 190 and an image-intensified CCD camera (not shown).

To demonstrate the use of these microchannel devices, two different types of DNA were introduced into the reservoirs, a potential difference was applied, and the velocities of the molecules through the region 126 were measured. To allow simultaneous observation of two different DNA molecule types using a single fluorescent dye, molecules sufficiently different in size were chosen so that the identity of the molecules could be determined by the fluorescence yield in the optical microscope. For this demonstration, 43 kilobase (kb) lambda phage DNA and 7.2 kb M13mp8 phage were observed simultaneously. Both molecules are plasmid DNA, but the lambda DNA has been cut into a linear strand, while the M13mp8 DNA is still circular. The two types of DNA were both stained with YOYO-1 (Molecular Probes) at a concentration of 1 dye molecule per 10 base pairs and then diluted to 0.5 $\mu$g/ml DNA in 0.5× tris-borate EDTA (ethylenediamene tetra-acetic acid) buffer with 2% mercaptoethanol added to prevent photobleaching. The solution was injected at both reservoir.

Although the silicon devices 152 have hydrophilic interiors and thus spontaneously fill with liquid when submerged, when they were sealed into the fluid interconnect package, trapped air prevented the water column from reaching the device. For this reason it was necessary to load the devices under vacuum. Even with vacuum loading, some bubbles were incorporated, but because the buffer solutions were degassed during the vacuum pumping, most bubbles trapped in the device dissolved into the buffer and were eliminated. DNA velocities were recorded for applied potentials ranging from 2–20 V across the 15 mm-long channel. The velocity was measured by recording the time required for individual molecules to traverse a 100 $\mu$m section of the dense pillar region 126.

Figure 15:
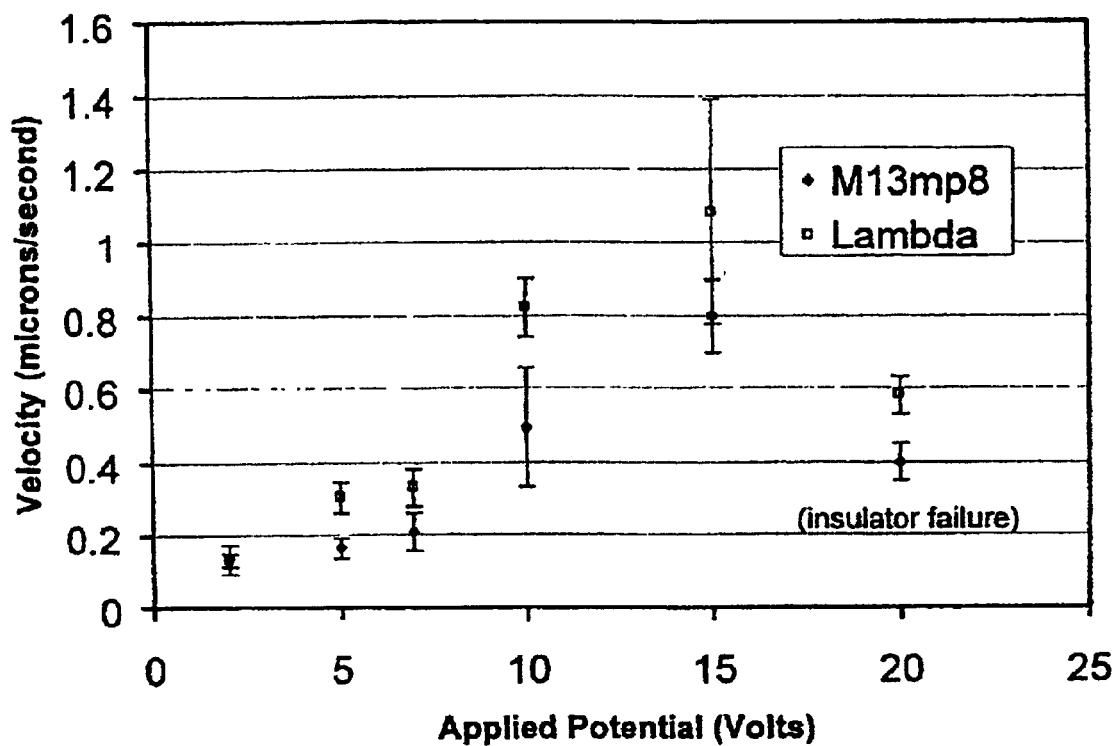
FIG. 15 is a chart illustrating the velocity of two difference molecule types for various applied potentials measured in apparatus fabricated in accordance with the present invention.

Observations of the two different strand lengths were made side-by-side and at the same time. To minimize the effect of boundary dogging, the field was periodically reversed, and occasionally the potential was increased briefly to assist molecules stuck at the boundary in overcoming the entropic barrier to entering the dense pillar region 126. The velocity comparison between the two strand types was reliable at a given potential because both molecule types were experiencing the same field. The M13mp8 DNA molecules were observed to have a significantly lower velocity than the larger lambda phage DNA for applied potentials of 5, 7, 10 and 15 volts. At 20 volts there was evidence that the dielectric insulating layers had failed and that the device was being short-circuited by conduction tough the substrate. FIG. 15 is a chart showing the velocity as a function of applied potential for both molecule types studied here. Each data point is the mean of several single-molecule observations. The ratio of velocities was largest for an applied potential of 5 volts, for which the lambda phage DNA moved 1.8 times faster than the M13mp8 phage DNA.

The error bars for each data point reflect the standard deviation of the single molecule observations. As such, the deviation reflects on band-broadening mechanisms that would determine the resolution in DNA separation. Other processes, such as field fluctuations and measurement errors, will also contribute to the variation in the measurements, so the resolution figure extracted from the distribution should be interpreted as a lower bound on the intrinsic resolution of the process. Taking h/2$\sigma$ as the resolution, where h is the band separation and $\sigma$ is the half-width of the band, this system shows a resolution of 118 per root-meter between the two molecule types working at 7 volts.

Figure 16:
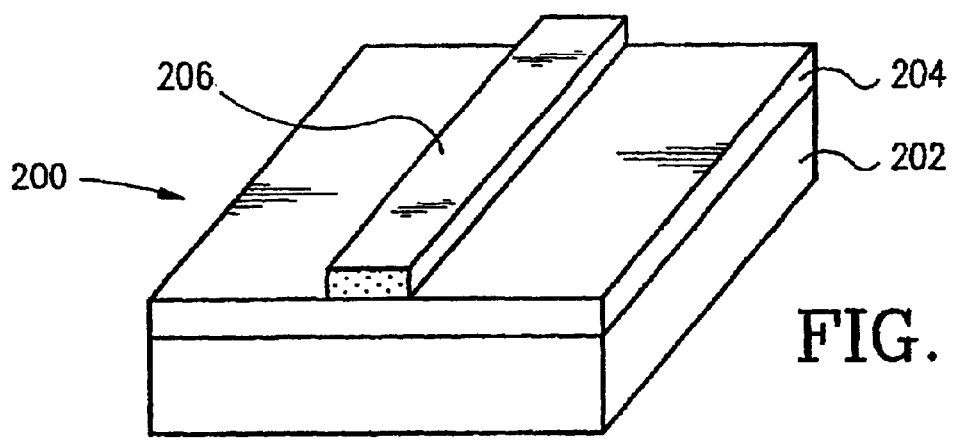
FIGS. 16–19 are diagrammatic illustrations of the steps of a method for fabricating multiple level structures on a single substrate.
Figure 17:
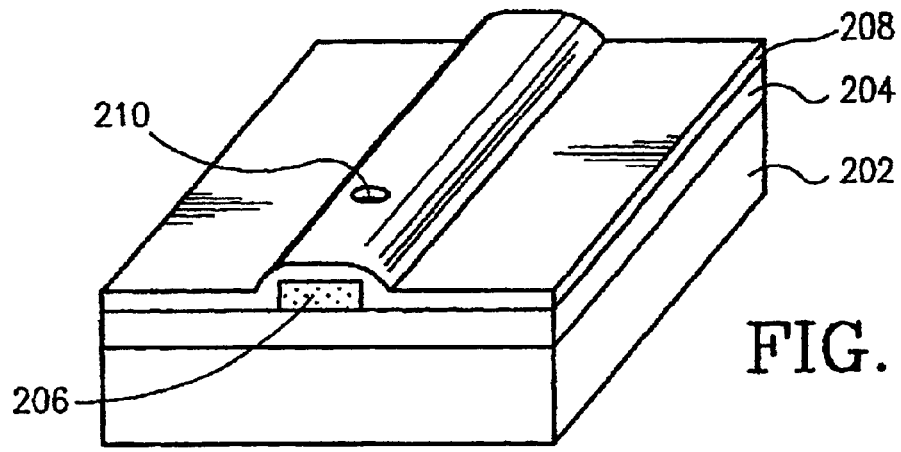

In a third embodiment of the invention, multi-level microchannel devices may be constructed utilizing the techniques described above. The process for fabricating such devices is an extension of the single-level fabrication techniques which have been described above, and this extension is illustrated in FIGS. 16–19, to which reference is now made. FIG. 16 illustrates a first stage in the fabrication of a multi-level microchannel device 200 formed on a wafer, or substrate 202. A bottom layer 204 of a permanent material such as an oxide or other dielectric material is deposited on the substrate, and a sacrificial layer 206 is deposited on the bottom layer, as described with respect to FIG. 1. Following patterning of the sacrificial layer 206, a layer 208 is applied, as previously described, providing a firs ceiling layer for the working gap, or microchannel that will be provided when the sacrificial layer 206 is removed. In this case, however, instead of perforating the ceiling layer 208 for removal of the sacrificial layer, as previously described, one or more vertical interconnect holes or apertures 210 may be provided in layer 208 where a vertical connection is to be made between the sacrificial layer 206 and corresponding sacrificial layers on second or subsequent levels. The vertical interconnect holes 210 are made using the same steps outlined above for making access holes for sacrificial layer removal, but are located so as to be aligned with corresponding structures in a second level. The layer 208 is optically transparent, and thus is of a suitable material such as silicon dioxide.

Figure 18:
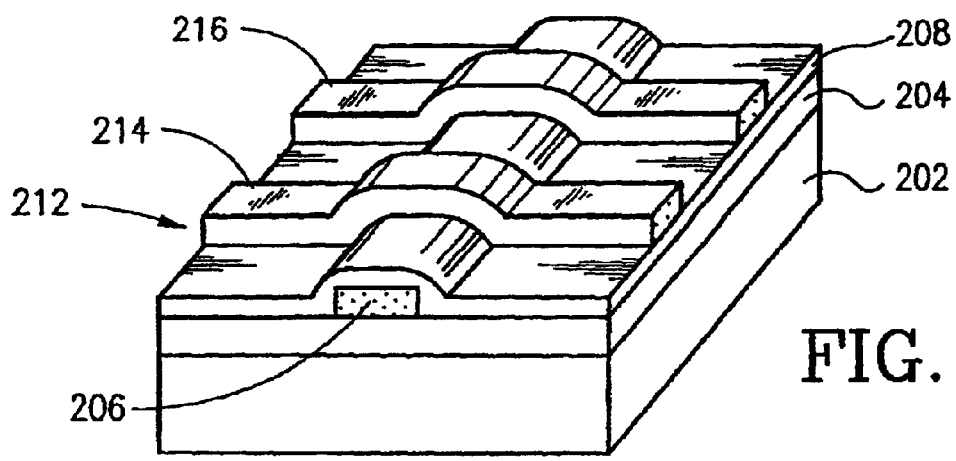

In the illustrated embodiment , instead of removing the sacrificial layer 206, a second sacrificial layer 212 is deposited on the top surface of the ceiling layer 208, in the manner previously described, and as illustrated in FIG. 18. This second sacrificial layer 212 is deposited to a thickness of between 30 nm and 1000 nm, and photolithography or electron beam lithography is used to pattern it, in the manner described above. FIG. 18 illustrates the second patterned sacrificial layer as including structural components in the form of two generally parallel tubes, or microchannels 214 and 216 on top of layer 208, with one tube 214 passing over the vertical interconnect hole 210 and the other passing over microchannel 206 in an area where there is no hole 210. The first and second sacrificial layers 206 and 212 make contact with each other where the vertical interconnect holes breach the fit level ceiling layer 208, as at hole 210, but are otherwise separated by layer 208. If desired, all structural components of the second layer may be in contact with corresponding components of the first layer; alternatively only some may be in contact through selectively placed vertical interconnect holes, or there may be no contact between layers.

Figure 19:
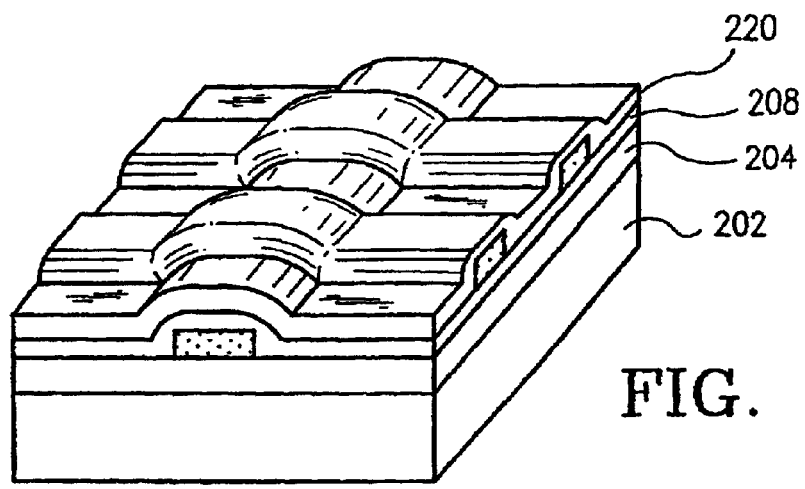
Figure 19A:
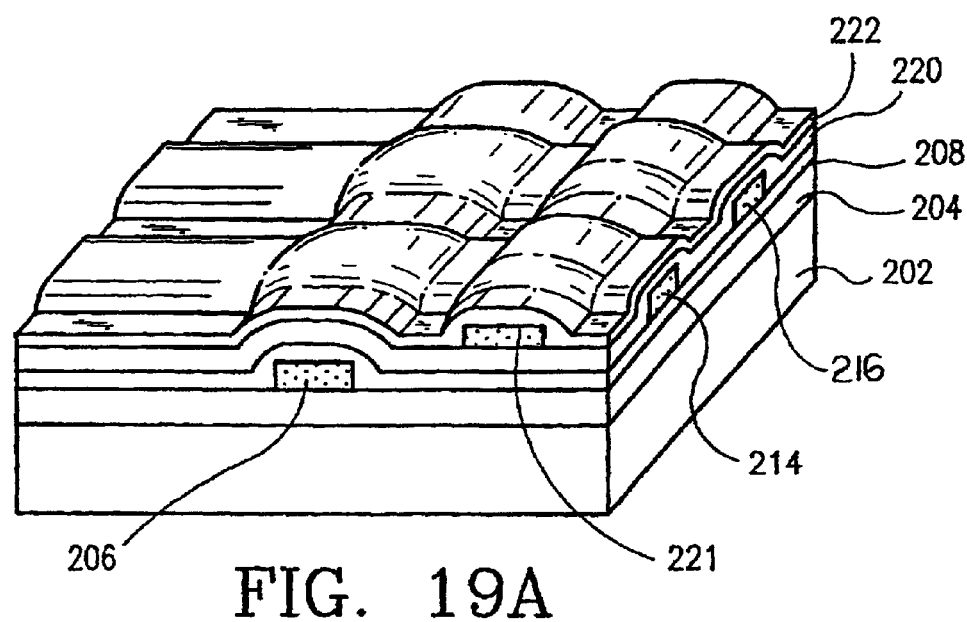
FIG. 19A illustrates a three-level structure on a single substrate fabricated by the process of the present invention as illustrated in FIGS. 16–19.

As illustrated in FIG. 19, a second level ceiling layer 220 is deposited over the top of the wafer to cover the components defined in the second sacrificial layer 212. If this is the last layer to be provided, then appropriate access holes as well as loading and exit apertures will be defined as previously described. If additional layers are desired, as illustrated in FIG. 19A, additional vertical interconnect holes may be provided in the layer 220 at selected locations, followed by a third sacrificial layer 221 and a third level ceiling layer 222. Additional layers may be provided as desired, and the final layer may be provided with irrigation access holes for removal of the sacrificial layers on all levels through the microchannels and vertical interconnect holes. Alternatively, the sacrificial layers may be accessed individually by fabricating tubes which intersect edges of the wafer.

Figures 20, 21:
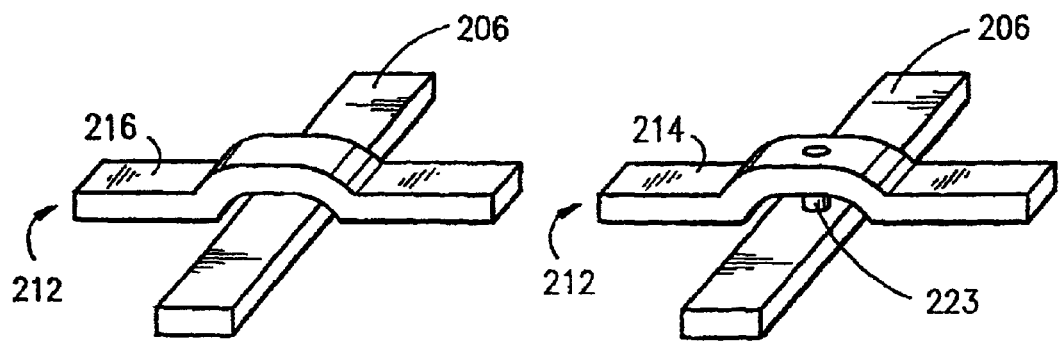
FIGS. 20 and 21 are diagrammatic illustrations of examples of multiple sacrificial levels produced in the process of FIGS. 16–19.

FIGS. 20 and 21 diagrammatically illustrate the selectable separation and interconnection of the sacrificial layers 206 and 212 by selecting the location of the vertical interconnect holes 210. FIG. 20 illustrates the crossing of the sacrificial material which will form microchannels 206 and 216 on two adjacent levels, where there is no connection between the two sacrificial layers, while FIG. 21 illustrates the crossing of microchannel 212 on one level over microchannel 206 on an adjacent level, illustrating the connection 222 extending through vertical interconnect hole 210. FIGS. 20 and 21 show the microchannels with the permanent layers removed for purposes of illustration, but it will be understood that when the layers 204, 208 and 220 are in place, the sacrificial material defining microchannel 206 will be isolated from the sacrificial material defining microchannel 212, while the material in microchannels 206 and 214 will be interconnected through connector 222. When the sacrificial layers are removed, the top and bottom permanent layers in each level remain, leaving hollow fluid flow microchannels, with fluid in channel 206 being able to flow into channel 214, but not into channel 216, in the illustrated example.

The multi-level fabrication technique described with respect to FIGS. 16–21 has many applications. As an example, it may be used to construct a 2-level combinatorial chemistry reactor such as that generally illustrated at 230 in FIG. 22. The reactor 230 includes, for example, 6 input microchannels 232 through 237, each of which passes over (or under, if desired) a single outlet, or drain microchannel 240, without interconnection, as illustrated at the intersection 242. These overpasses are fabricated in a manner similar to the fabrication of microchannels 206 and 216, described above and illustrated, for example, in FIG. 20. Each of the input channels is also connected to the drain 240 by way of interconnects such as that illustrated at 244, each interconnect being fabricated in the manner described with respect microchannels 206 and 214, illustrated in FIG. 21, for example. The drain 240 leads to an outlet, indicated by arrow 245, while the input channels 232–237 all lead to a common reaction chamber 246 which, in turn, is connected to a fluid outlet microchannel 248. Voltages applied at any of the fluid terminals of the device will induce flow in the system via electroosmosis.

In the operation of a typical device, a steady flow of fluid is maintained from each of the 6 input microchannels to the drain microchannel 240 by maintaining the outlet 245 of the drain at a low potential. This serves, for example, to prevent cross contamination of the fluids in each of the input channels by creating a small, constant flow from each of the inputs 232–237 to the drain outlet 245. The drain line 240 passes under (or over) all six of the fluid input microchannels and makes a vertical interconnect with each channel upstream from the reaction chamber 246, as at interconnect 244. Multiple levels are required for this device, since it is topologically impossible to provide a common drain for multiple channels in a single level.

Figure 22:
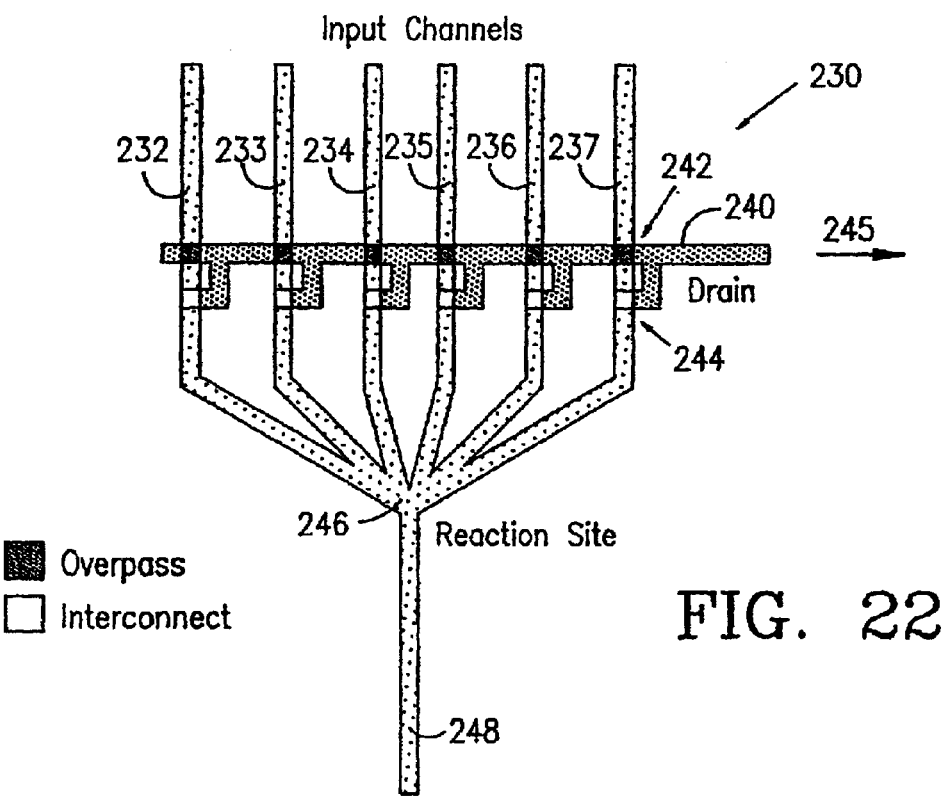
FIG. 22 is a diagrammatic illustration of a sub-femtoliter mixing system fabricated by the multiple level process of the invention.

To inject fluid from one of the input microchannels 232–237 to the reaction site 246, a higher voltage is applied to the selected input channel so that fluid flows to both the drain 240 and the reaction site 246 for that channel. With this arrangement, reagents supplied through the input channels can be kept only a few microns from the reaction site 246 and at the same time remain clean. The device illustrated in FIG. 22 is a prototype for a general purpose reactant mixing system, but natural extensions of this concept will permit mixing of reagents in any order and any time sequence, and will allow the injection of heat and light at any point in the device through the optically transparent ceiling layer. Any substance that can be synthesized using only liquid ingredients and modification by heat and light could be produced in sub-femtoliter quantities in a device of this type, utilizing the microchannels of the present invention.

Another application of the process of the present invention is the fabrication of microchannels having widths and heights as small as about 10 nm. The controlled fabrication of channels in the form of tubes with such dimensions opens new prospects for science, since the physical characteristics of fluid columns and such thin channels win be different from those in conventional capillaries. Decreased volume-to-surface-area ratios for small channels means that the interaction between the channel walls and the fluid will be more important, and surface effects will be crucial factors in fluid flow.

Although advanced electron beam lithography can be employed to produce structures having lateral dimensions as small as about 20 nm, two methods for providing microchannels with lateral and vertical dimensions smaller than 10 nm are available using the techniques of the present invention. The first method uses thin film deposition over a step edge so that the lateral dimensions of the microcapillary are determined by the thickness of the film. A second technique uses thermal oxidation of polysilicon to reduce the dimensions of a microchannel which has been defined using conventional lithography.

Figure 23:
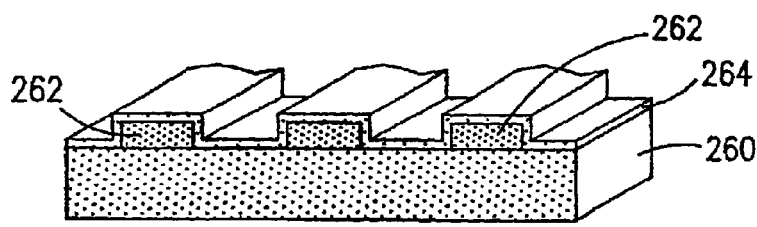
FIGS. 23–25 are diagrammatic illustrations of a step-edge deposition process for fabricating ultra-small diameter capillaries.
Figure 24:
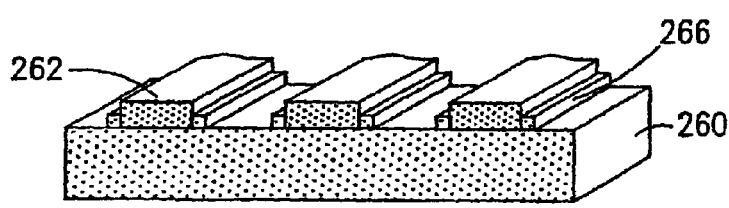
Figure 25:
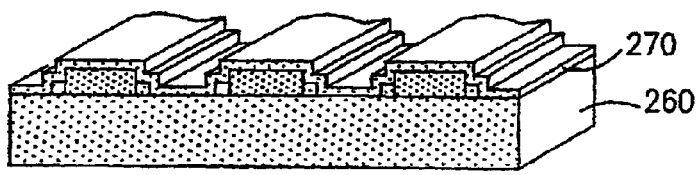

FIGS. 23, 24 and 25 illustrate a step edge deposition technique for fabricating a nanometer scale capillary, or nanochannel. In FIG. 23, a substrate 260, which preferably is a dielectric material such as silicon nitride or silicon dioxide, is patterned, by photolithography or electron beam lithography, and is etched with RIE to produce one or more ridges 262. Such a process provides corners on the ridges having near atomic sharpness, with the ridges having substantially vertical sidewalls. Thereafter, a sacrificial layer 264 of a conformal thin film of CVD polysilicon or amorphous silicon is coated over the patterned silicon base 260. Films as thin as 10 nm can be deposited to a tolerance smaller than 1 nm, and the thickness of the film can be used to control the vertical dimension of a channel in the manner described above in the previous embodiments. The layer 264 is deposited to a substantially uniform thickness except in the corners at the bases of the ridges 262, where the layer accumulates to a greater thickness. In order to establish the lateral dimension of the capillary, a subsequent unmasked RIE is used to remove the film 264 everywhere except where the step in the substrate has caused an increase in the thickness of the film. This is illustrated in FIG. 24 by the small amount of film material 266 remaining at the base of each of the ridges 262 after the RIE step. This remaining material 266 forms thin sacrificial wires that extend along the bases of each of the ridges and since the film thickness controls the width of the wire and the RIE etch depth controls its height, both dimensions of the wire can be controlled to dimensions smaller than 10 nm.

Thereafter, a ceiling layer 270 is deposited over the top surface of the substrate 260, covering the ridges 262 and the sacrificial wires 266. Perforations are provided in the layer 270 to permit access to the wires 266, and the sacrificial layer is removed by a wet etch process as previously described. Thereafter, the access holes are closed by a sealing layer to provide enclosed nanochannels. The perforations for removal of the sacrificial layer preferably are made at the ends of the tubes to prevent clogging during the sealing.

Figures 26, 27:
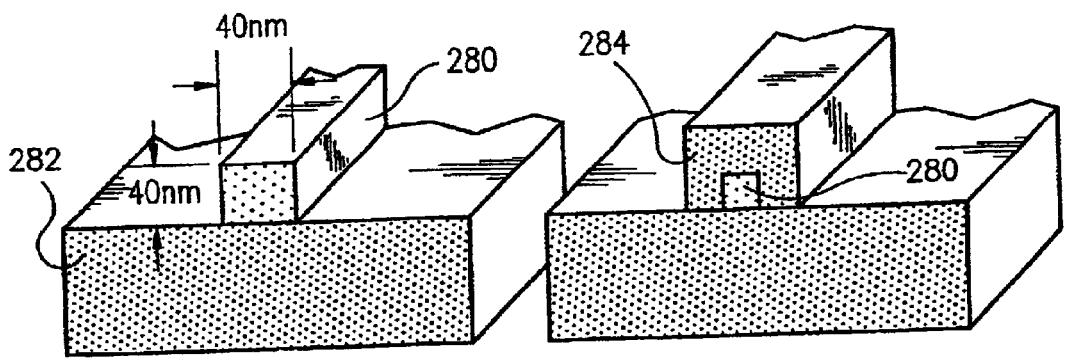
FIGS. 26 and 27 illustrate a second process for fabricating ultra-small diameter capillaries.

A second method for producing nanochannels is illustrated in FIGS. 26 and 27, wherein oxidative restriction is used to reduce the size of a sacrificial polysilicon or amorphous silicon wire patterned onto a flat surface. In this process, a wire 280 is formed by depositing a sacrificial layer of polysilicon or amorphous silicon on the top surface of a silicon base 282. The layer has a thickness of approximately 40 nm, and is patterned by conventional electron beam lithography to a lateral dimension of about 40 nm. Thereafter, the patterned wire 280 is subjected to thermal oxidation to reduce the width and height of the wire by consuming silicon from the surface to form a silicon dioxide coating 284, leaving the reduced wire 280 (FIG. 27). The oxide 284 can then be removed, or left in place to serve as the capillary wall and the application of ceiling layers, (if desired), perforations and removal of the sacrificial layer are performed as previously described.

Capillaries having dimensions on the order of 10 nm fabricated by one of the above-described techniques may be used for a wide variety of purposes. The dimensions of the tube are so small that single molecule sensitivity is required to detect flourescent molecules. The dimensions of such channels are comparable to the average pore size of other porous materials such as gels, and such channels could thus be used as a filter to remove larger molecules from solution. Since the techniques described permit fabrication of channels with a specific depth or width, sophisticated filters can be designed.

Figure 28:
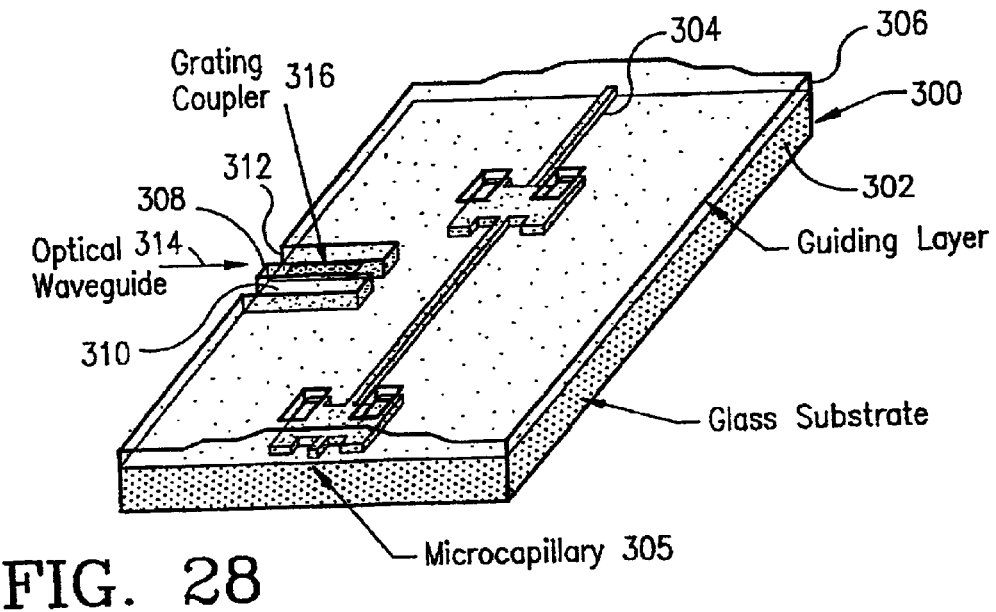
FIG. 28 is a diagrammatic perspective view of an integrated microcapillary and waveguide device using the sacrificial layer process of the present invention.
Figure 29:
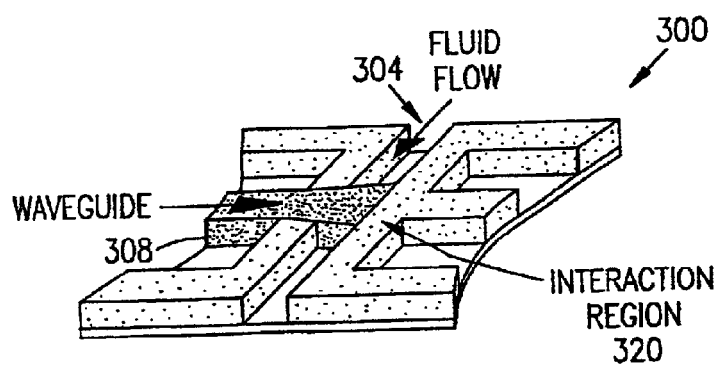
FIG. 29 is an enlarged view of a portion of the device of FIG. 28.

A feature of the process of the present invention is that it provides a technique for interconnecting fluidic structures and devices not only with each other, but with non-fluidic devices which maybe fabricated on a common substrate using compatible materials and procedures. One such application of the process described herein is the provision of a microchannel-based fluid flow system having integrated planar waveguide optics on the same substrate as the fluidic circuitry. Such a unified structure is of vital interest in the development of complex analysis systems on a single chip which will require not only manipulation of fluids but also acquisition and processing of data. Not only is the method of fabricating an integral waveguide structure compatible with the microfabrication process of the invention, but the small dimensions of the fluidic channel fabricated by the present process provides significant advantages over prior optical detection systems for fluid channels. For example, the integral structure and the small size reduces fluorescence background to a degree that will allow, for the first time, fluorescence correlation spectroscopy (FCS) of samples at near biological concentrations, thereby opening the possibility of applying FCS as an analytical tool directly to biological fluids., An example of a microchannel fluidics system with integrated waveguide optics is illustrated at 300 in FIGS. 28 and 29. The system 300 includes a glass substrate 302 on which is deposited a sacrificial layer 304 which is patterned in the shape of a microchannel 305, in the manner described above. A dielectric ceiling layer 306 is placed over the patterned sacrificial layer 304; thereafter, a planar waveguide 308 is fabricated in the ceiling layer using conventional photolithographic or electron beam lithography techniques as discussed above. The high refractive index ceiling material 306 serves as the optical guide medium. The waveguide is a ridge of the dielectric material 306 formed by etching grooves 310 and 312 on each side of the waveguide 308 during the same etching step in which perforation holes are defined in the ceiling layer 306 for use in removing the sacrificial layer. When the perforations are resealed (as described above), the lower refractive index resealing layer also films in the grooves 310 and 312 and covers the top surface of the waveguide 308, so that this material surrounds three sides of the waveguide and serves as a cladding for it. The lower index glass substrate 302 provides the fourth wall for the waveguide. Light injection into the waveguide can be obtained directly by end coupling from a light source on the chip, as indicated by arrow 314 in FIG. 28, or can be obtained by patterning a diffractive coupler grating 316 in one of the CVD With the foregoing fabrication technique, the waveguide 308 is aligned to intersect the microchannel 304 (See FIG. 29), with the intersection of the two micron-sized fluidic and optical elements defining an interaction region 320 having a sub-femtoliter volume. The optical waveguide may be used to provide light excitation to fluorescent solutions carried in the microchannels 304, as for use in fluorescence correlation spectroscopy.

The fabrication of the waveguide proceeds as follows. In a first step, a layer of 250–300 nm thick undoped polysilicon is deposited on a fused silica substrate. Fused silica is used because of its index of refraction, Its low defect density, its absence of background fluorescence and its compatibility with CMOS processing rules. The polysilicon is capped with a 100 nm thick layer of thermally grown silicon oxide to be used as a hard mask during the pattern transfer of the first lithography step.

The first lithography steep is used to define the future shape of the microfluidic portion of the device. In one embodiment, the tube is 10 micrometers wide across most of the length of the device except in the interaction region where it is narrowed to 1 micrometer. High aspect ratios are directly possible with this method; aspect ratios of up to 100:1 have been demonstrated. The photolithography is performed on an I-line stepper with final resolution of 0.5 micrometer in 1.2 microns of photoresist. The pattern is then transferred to the silicon oxide hard mask in a short $CHF_3/O_2$ dry etch. The resist is then stripped in a 15 minutes $O_2$ plasma by a barrel etch. The polysilicon is finally patterned using a $Cl_2/BCl_3/H_2$ plasma RIE. This plasma is used to get a high selectivity between oxide and silicon, which avoids overetching into the substrate.

After this, the device is covered by a 1.1 micrometer thick ceiling, or top layer of PECVD silicon dioxide. The temperature and power of the system are tuned to obtain a layer of slightly out of stoichiometry oxide with a refractive index around 1.52. It is this layer that will form the core of the ridge waveguide that will be used for light delivery. All other layers will have a lower index. Because of the lower temperature at which this process is run, special care for the cleanliness of the sample is extremely important.

Once this ceiling layer has been deposited over the patterned sacrificial polysilicon layer, the second level of lithography is performed. The ridge waveguide and the access holes are patterned in two micrometers of photoresist. The access holes are the holes that will be used to give TMAH access to the sacrificial polysilicon during the final removal step. The pattern is then transferred into the PECVD oxide using again the $CHF_3/O_2$ plasma RIE. In this step, overetching is not an issue while underetching would prove catastrophic to the device. The photoresist is stripped clean, using a sulfuric/water solution, and a new level of photolithography is performed, this time defining the gratings that will be used to couple light from the laser to the waveguide. After that, the sample is immersed in a hot bath of TMAH for 6 hours to remove the polysilicon and to produce the working gap previously described. The etch rate of the sacrificial layer of polysilicon in TMAH is lower than the bulk value because of its confinement in the microchannel system. The process is partially limited by the time it takes for the chemicals to renew themselves by diffusion out of the capillaries.

In a final deposition step, a 1.5 micrometer thick sealing layer of VLTO oxide is deposited by CVD. This oxide will reseal the access holes and cap the waveguide with a layer of index 1.46, VLTO oxide, which is particularly convenient since the low temperature of the process (475° C.) minimizes the application of thermal stress to the system, and the partial conformality of the VLTO furnace guarantees a good seal of the access holes. At this point, the system is completely sealed and the working gap cavities are closed.

The final lithography step is to etch final access holes at the extremities of the working gap cavities. For this, 10 micrometers of photoresist is patterned with two large (500 micrometers by 500 micrometers) holes that are etched through the sealing layer and the top, or ceiling layer, to intersect the microchannel in the usual $CHF_3/O_2$ plasma RIE. The photoresist is then stripped in an $O_2$ plasma and the device is ready for use.

The foregoing fluidics and optical waveguide system 300 addresses some of the limitations of conventional fluorescence correlation spectroscopy (FCS). First, for a channel having a cross-sectional dimension of 0.1×0.1 micrometers, and a mode size at the output of the waveguide of 1.5 micrometers, the interaction volume 320 is as small as $15 \times 10^{-18}$ liters. This is well below the limits of classical optics to which FCS is subjected. Both the background noise and the average number of molecules in the interaction volume are significantly decreased, compared to conventional FCS, and the decreased interaction volume means that the average number of molecules in it is significantly decreased. This opens to FCS a new range of reactions to fluorescence correlation spectroscopy studies.

The confinement of a molecule inside a microchannel presents another advantage, for since the flow is fully constrained in the channel, all of the solution is probed. Thus, no molecule will escape detection by diffusing out of the interaction region. This decreases measurement time while maintaining statistical accuracy of the measurement. This is of crucial importance in single molecule sequencing, where the probability of a false negative must be maintained as low as possible.

Figure 30:
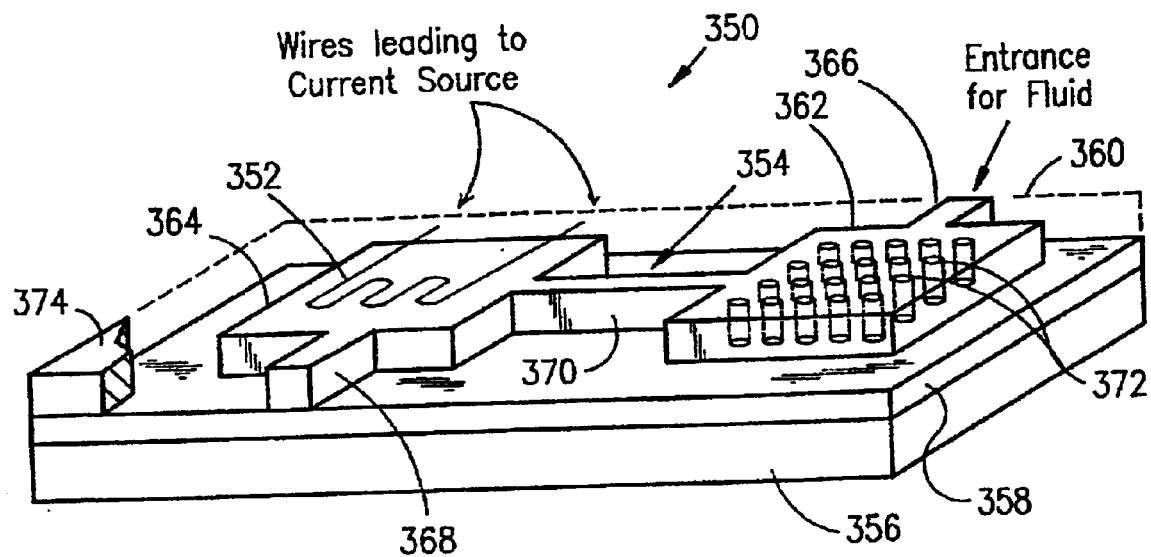
FIG. 30 is a partial perspective view of an integrated electrical heating element in a fluidic system.
Figure 31:
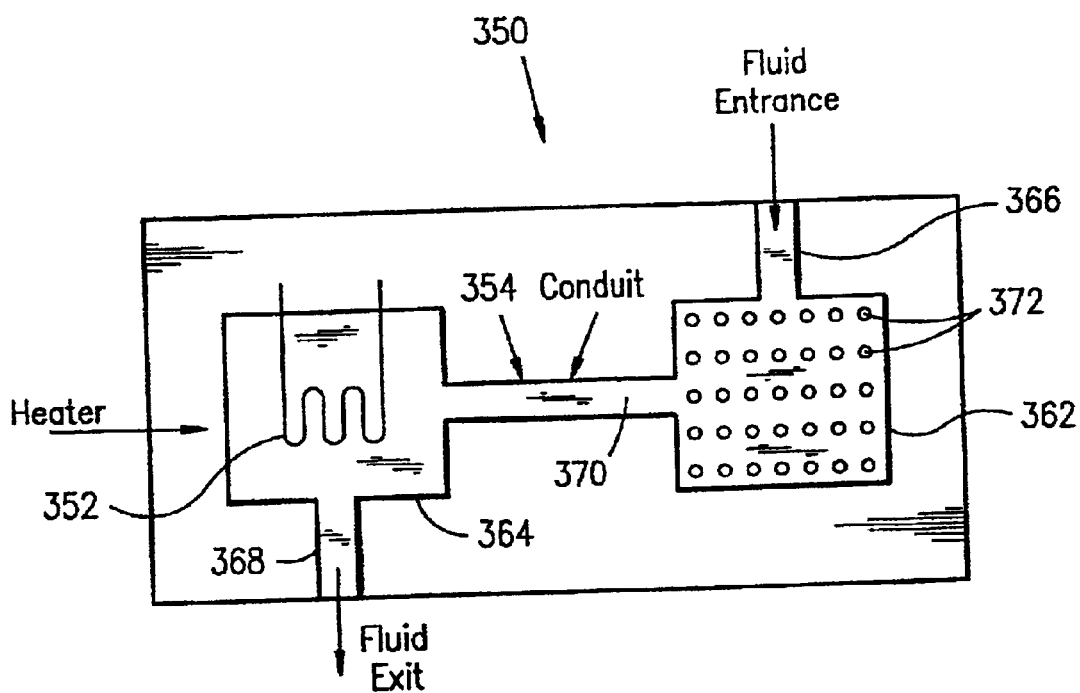
FIG. 31 is a top plan view of the structure of FIG. 30.

FIGS. 30 and 31 illustrate another example of the use of the process of the present invention in the fabrication of an integrated system 350, wherein an electronic device 352, such as an electrical resistance which may serve as a heater or a sensor, is incorporated in a microchannel structure 354. The system 350 is fabricated on a substrate 356 on which is deposited a floor layer 358 of a permanent material such as a suitable dielectric oxide. The resistor element 352 is positioned on the substrate, and a sacrificial layer 360 (illustrated by dotted lines) is deposited on layer 358, and is patterned as described above to form two chambers 362 and 364, inlet and outlet microchannels 366 and 368, and connector microchannel 370 extending between chambers 362 and 364. The chamber 362 is further patterned to include an array of holes 372. Thereafter, a ceiling layer 374, partially cut away in the illustration of FIG. 30 and omitted from FIG. 31, is deposited over the patterned sacrificial layer and over the portion of layer 358 exposed by the patterning of the sacrificial layer. The ceiling layer enters the holes 372 to form closely spaced pillars in chamber 362. Finally, the sacrificial layer is removed, as previously described, to form the microchannel structure 354 between the floor and ceiling layers 358 and 374, respectively. The pillars form obstacles to fluid flow through chamber 362, acting as a sieve or an artificial gel filter for fluid flowing through the system. The resistor element is located in chamber 364 and is contact with the fluid.

The present invention provides a new ability to design and build integrated fluidic and optical circuits and provides the opportunity for new approaches to single molecule studies, polymer dynamics, and fluid dynamics. The multilevel microfluidic system is integrated on a single chip and represents a significant contribution towards a fully integrated chemical reactor. The nanochannel described herein creates an opportunity to study mesoscopic phenomena in solutions and can be used to study the behavior of macromolecules in confined spaces. The present invention also provides the ability to guide light with integrated optics in the same system as a fluidic system to enable photo-detection, photo-chemistry and spectroscopy to be integrated with complex fluidic and electronic systems, leading to the possibility of a wide range of analytical devices on a single chip. Although the invention has been described in terms of preferred embodiments, it will be apparent that numerous modifications and variations may be made without departing from true spirit and scope thereof, as set forth in the following claims.

What is claimed is:

1. A method for fabricating a fluidic system, comprising:
   depositing a floor layer on a first surface of a substrate;
   depositing a silicon based sacrificial layer on the first surface of said floor layer;
   patterning said silicon sacrificial layer to define in the silicon sacrificial layer the shape of a desired fluid working gap;
   depositing a ceiling layer to cover said silicon sacrificial layer;
   patterning and etching said ceiling layer to form a ridge waveguide intersecting the location of a desired fluid working gap;
   patterning and etching said ceiling layer to define at least one access hole leading to said sacrificial layer; and
   removing said silicon sacrificial layer from between said floor layer and said ceiling layer by etching to produce said working gap.

2. The method of claim 1, wherein removing said silicon sacrificial layer includes:

providing at least one access hole leading to said silicon sacrificial layer; and etching said silicon sacrificial layer through said at least one access hole.

3. The method of claim 2, wherein providing said at least one access hole includes forming at least one hole through said ceiling layer to said silicon sacrificial layer.

4. The method of claim 3, further including depositing a sealing layer over said ceiling layer to close said at least one access hole.

5. The method of claim 1, wherein patterning includes:

defining in said sacrificial layer the boundaries of a fluid chamber working gap; and defining within the boundaries of said fluid chamber a multiplicity of holes extending through said silicon sacrificial layer to said floor layer.

6. The method of claim 5, wherein depositing said ceiling layer includes depositing the ceiling layer in said multiplicity of holes to define obstacles in said working gap.

7. The method of claim 6, wherein removing said silicon sacrificial layer includes etching said silicon sacrificial layer between said obstacles in said working gap to produce an artificial gel.

8. The method of claim 7 wherein the obstacles are approximately 100 nanometers in diameter.

9. The method of claim 1 wherein the sacrificial layer is deposited using chemical vapor deposition.

10. The method of claim 1, further including fabricating on said substrate a device for interconnection with said working gap.

11. The method of claim 10, wherein fabricating said device is carried out by a process compatible with the process of fabricating said working gap.

12. The method of claim 11, further including interconnecting said working gap with said device to allow fluid transfer between said gap and said device.

13. A method for fabricating a multilevel fluidic device, comprising:

forming a first floor layer; depositing a first sacrificial layer on a first surface of said floor layer;

patterning said sacrificial layer to define in the sacrificial layer the shape of a desired fluid working gap;

depositing a ceiling layer to cover said sacrificial layer;

patterning said second sacrificial layer to define in the second sacrificial layer a second desired fluid gap;

depositing a second ceiling layer to cover said second sacrificial layer; and after depositing one of the ceiling layers;

patterning and etching said ceiling layer to form a ridge waveguide intersecting the location of a desired fluid working gap;

patterning and etching said ceiling layer to define at least one access hole leading to said sacrificial layer; and removing said sacrificial layers to produce multilevel working gaps wherein at least one of the sacrificial layers is a silicon material.

14. The method of claim 13, further including depositing additional patterned sacrificial and ceiling layers sequentially to produce additional working gap levels.

15. The method of claim 14, further including producing at least one vertical connector hole through a ceiling layer to interconnect adjacent sacrificial layers.

16. The method of claim 15, further including producing at least one vertical connector hole through each ceiling layer that receives a sacrificial layer on each level to the sacrificial layer on a next adjacent layer.

17. The method of claim 16, wherein removing said sacrificial layers includes:

providing at least one access hole leading to at least one of said sacrificial layers; and etching all said sacrificial layers through said at least one access hole and said at least one vertical connector between each level.

18. The method of claim 17, wherein providing said at least one access hole includes forming at least one access hole through the topmost ceiling layer to the sacrificial layer covered by said topmost ceiling layer.

19. The method of claim 18, further including depositing a sealing layer over said second ceiling layer to close said at least one access hole.

20. The method of claim 13, wherein patterning includes:

defining in at least one of said sacrificial layer and said second sacrificial layer the boundaries of at least one fluid chamber working gap; and defining within the boundaries of said at least one fluid chamber a multiplicity of holes extending through a corresponding sacrificial layer.

21. The method of claim 20, wherein depositing said first and second dielectric ceiling layers includes depositing the ceiling layer in said multiplicity of holes to define obstacles in said at least one fluid working gap.

22. The method of claim 21, wherein removing said sacrificial layer and said second sacrificial layer includes etching said between said obstacles in said at least one working gap to produce an artificial gel.

23. A method for fabricating a nanochannel, comprising:

patterning and etching a substrate to produce a surface having a vertical sidewall intersecting the substrate at the base of the sidewall;

depositing a thin film conformal sacrificial layer on said substrate and covering said sidewall, the thickness of the thin film at the base of the sidewall having an increased thickness and width to form a sacrificial wire along the base;

removing by an unmasked RIE the thin film sacrificial layer on the sidewall and on the substrate, while leaving said sacrificial wire along said base;

depositing a ceiling layer on said substrate and said sidewall and covering said wire; and removing said sacrificial wire to produce a nanochannel between said substrate, sidewall, and ceiling layer.

24. A method for forming a nanochannel, comprising:

depositing a thin film silicon sacrificial layer on a substrate;

patterning said silicon layer to define a sacrificial wire having the shape of a desired nanochannel;

oxidizing the patterned sacrificial silicon layer to reduce the width and height of the sacrificial wire bay consuming silicon from the surface of the wire to form a silicon oxide coating; and removing the sacrificial wire from within said silicon oxide coating to produce a nanochannel.

* * * * *